(12) United States Patent
Alghooneh et al.

(10) Patent No.: US 10,564,725 B2
(45) Date of Patent: Feb. 18, 2020

(54) HAPTIC EFFECTS USING A HIGH BANDWIDTH THIN ACTUATION SYSTEM

(71) Applicant: IMMERSION CORPORATION, San Jose, CA (US)

(72) Inventors: Mansoor Alghooneh, Toronto (CA); Robert Lacroix, Saint-Lambert (CA); Juan Manuel Cruz-Hernandez, Montreal (CA); Neil Olien, Montreal (CA); Vahid Khoshkava, Montreal (CA)

(73) Assignee: IMMERSON CORPORATION, San Jose, CA (US)

( * ) Notice: Subject to any disclaimer, the term of this patent is extended or adjusted under 35 U.S.C. 154(b) by 0 days.

(21) Appl. No.: 15/928,010

(22) Filed: Mar. 21, 2018

(65) Prior Publication Data

US 2018/0275759 A1 Sep. 27, 2018

Related U.S. Application Data

(60) Provisional application No. 62/475,544, filed on Mar. 23, 2017.

(51) Int. Cl.
*G06F 3/01* (2006.01)
*G06F 3/041* (2006.01)

(52) U.S. Cl.
CPC .............. *G06F 3/016* (2013.01); *G06F 3/041* (2013.01)

(58) Field of Classification Search
CPC ....................................................... G06F 3/016
See application file for complete search history.

(56) References Cited

U.S. PATENT DOCUMENTS

| | | |
|---|---|---|
| 6,629,341 B2 | 10/2003 | Wilkie et al. |
| 9,367,136 B2 | 6/2016 | Latta et al. |
| 9,370,459 B2 | 6/2016 | Mahoney |
| 9,370,704 B2 | 6/2016 | Marty |
| 9,392,094 B2 | 7/2016 | Hunt et al. |
| 9,462,262 B1 | 10/2016 | Worley, III et al. |
| 9,513,706 B2 | 12/2016 | Cruz-Hernandez et al. |
| 9,626,805 B2 | 4/2017 | Lampotang et al. |
| 9,645,646 B2 | 5/2017 | Cowley et al. |
| 9,652,037 B2 | 5/2017 | Rubin et al. |
| 9,760,166 B2 | 9/2017 | Ammi et al. |
| 9,811,854 B2 | 11/2017 | Lucido |
| 9,851,799 B2 | 12/2017 | Keller et al. |
| 9,933,851 B2 | 4/2018 | Goslin et al. |

(Continued)

FOREIGN PATENT DOCUMENTS

| | | |
|---|---|---|
| EP | 3093736 A1 | 11/2016 |
| WO | 2014117125 A1 | 7/2014 |

OTHER PUBLICATIONS

Smart Material, Macro Fiber Composite, Retrieved Nov. 23, 2016, from https://www.smart-material.com/MFC-product.main.html.

*Primary Examiner* — Michael Pervan
(74) *Attorney, Agent, or Firm* — Nath, Goldberg & Meyer

(57) ABSTRACT

Haptic feedback is provided by rendering haptic effects on a haptically-enabled device that includes a front screen, a back cover coupled to the front screen, and a haptic output device attached to or formed within the front screen or the back cover. The haptic output device is configured to render a high-definition (HD) vibratory haptic effect, a low-frequency vibratory haptic effect, and a deformation haptic effect.

17 Claims, 21 Drawing Sheets

(56) References Cited

U.S. PATENT DOCUMENTS

| | | |
|---|---|---|
| 9,948,885 B2 | 4/2018 | Kurzweil |
| 2007/0236449 A1* | 10/2007 | Lacroix ............ H04M 1/72522 345/156 |
| 2008/0319279 A1* | 12/2008 | Ramsay ................ A61B 5/486 600/301 |
| 2013/0207917 A1* | 8/2013 | Cruz-Hernandez ..... G06F 3/041 345/173 |
| 2014/0035735 A1 | 2/2014 | Zellers et al. |
| 2016/0070348 A1 | 3/2016 | Cowley et al. |
| 2016/0084605 A1 | 3/2016 | Monti |
| 2016/0086457 A1 | 3/2016 | Baron et al. |
| 2016/0163227 A1 | 6/2016 | Penake et al. |
| 2016/0166930 A1 | 6/2016 | Brav et al. |
| 2016/0169635 A1 | 6/2016 | Hannigan et al. |
| 2016/0170508 A1 | 6/2016 | Moore et al. |
| 2016/0171860 A1 | 6/2016 | Hannigan et al. |
| 2016/0171908 A1 | 6/2016 | Moore et al. |
| 2016/0187969 A1 | 6/2016 | Larsen et al. |
| 2016/0187974 A1 | 6/2016 | Mallinson |
| 2016/0201888 A1 | 7/2016 | Ackley et al. |
| 2016/0209658 A1 | 7/2016 | Zalewski |
| 2016/0214015 A1 | 7/2016 | Osman et al. |
| 2016/0214016 A1 | 7/2016 | Stafford |
| 2016/0375170 A1 | 12/2016 | Kursula et al. |
| 2017/0102771 A1 | 4/2017 | Lei |
| 2017/0103574 A1 | 4/2017 | Faaborg et al. |
| 2017/0131775 A1 | 5/2017 | Clements |
| 2017/0148281 A1 | 5/2017 | Do et al. |
| 2017/0154505 A1 | 6/2017 | Kim |
| 2017/0168576 A1 | 6/2017 | Keller et al. |
| 2017/0168773 A1 | 6/2017 | Keller et al. |
| 2017/0178407 A1 | 6/2017 | Gaidar et al. |
| 2017/0203221 A1 | 7/2017 | Goslin et al. |
| 2017/0203225 A1 | 7/2017 | Goslin |
| 2017/0206709 A1 | 7/2017 | Goslin et al. |
| 2017/0214782 A1 | 7/2017 | Brinda |
| 2017/0257270 A1 | 9/2017 | Goslin et al. |
| 2017/0352185 A1 | 12/2017 | Bonilla Acevedo et al. |
| 2018/0050267 A1 | 2/2018 | Jones |
| 2018/0053351 A1 | 2/2018 | Anderson |
| 2018/0077976 A1 | 3/2018 | Keller et al. |
| 2018/0081436 A1 | 3/2018 | Keller et al. |
| 2018/0093181 A1 | 4/2018 | Goslin et al. |
| 2018/0107277 A1 | 4/2018 | Keller et al. |
| 2018/0120936 A1 | 5/2018 | Keller et al. |

* cited by examiner

HAPTIC EFFECTS USING A HIGH BANDWIDTH THIN ACTUATION SYSTEM

PRIORITY APPLICATION

This application claims priority to U.S. Provisional Patent Application No. 62/475,544, filed on Mar. 23, 2017, the entire content of which is incorporated herein by reference.

FIELD

Embodiments are directed to providing haptic feedback using an actuation system, and more particularly, to providing haptic feedback by rendering haptic effects using a high bandwidth thin actuation system.

BACKGROUND INFORMATION

Portable/mobile electronic devices, such as mobile phones, smartphones, tablets, game controllers, personal digital assistants ("PDAs"), etc., typically include output mechanisms to alert a user of certain events that occur with respect to the devices. For example, a cell phone normally includes a speaker for audibly notifying the user of an incoming telephone call event. The audible signal may include specific ringtones, musical ditties, sound effects, etc. In addition, the cell phone can include a display screen that can be used to visually notify the user of incoming phone calls.

In some mobile devices, kinesthetic feedback (such as active and resistive force feedback) and/or tactile feedback (such as vibration, texture, and heat) is also provided to the user, more generally known collectively as "haptic feedback" or "haptic effects." Haptic feedback can provide cues that enhance and simplify the user interface. Specifically, vibration effects, or vibrotactile haptic effects, can be useful in providing cues to the user of an electronic device to alert the user to specific events, or provide realistic feedback to create greater sensory immersion within a simulated or virtual environment.

SUMMARY

One embodiment is directed to a haptically-enabled device that includes a front screen and a back cover coupled to the front screen of the haptically-enabled device. The device further includes an actuator attached to or formed within the back cover or the front screen. The haptic output device is configured to render a high-definition (HD) vibratory haptic effect, a low-frequency vibratory haptic effect, and a deformation haptic effect.

BRIEF DESCRIPTION OF THE DRAWINGS

Embodiments will be more clearly understood from the following detailed description taken in conjunction with the accompanying drawings.

FIG. 1 is a block diagram of a haptically-enabled mobile device/system used to implement one embodiment.

FIG. 2 illustrates a disassembled view of a mobile device in accordance with one embodiment.

FIG. 3 illustrates an exploded view of a mobile device in accordance with one embodiment.

FIG. 4 illustrates a side profile view of a mobile device in accordance with one embodiment.

FIG. 5 is a graph of measured peak to peak acceleration on the top-side of the outer surface of a mobile device in accordance with one embodiment.

FIG. 6 is a graph of measured peak to peak acceleration on the bottom-side of the outer surface of a mobile device in accordance with one embodiment.

FIG. 7 illustrates reference points on a front screen for the measurements in FIGS. 8 and 9 in accordance with embodiments.

FIG. 8 is a graph of measured peak to peak acceleration vs. frequency at different reference points on a front screen of a haptically-enabled device in accordance with one embodiment.

FIG. 9 is a graph of measured output frequency vs. frequency at different reference points on a front screen of a haptically-enabled device in accordance with one embodiment.

FIGS. 10 and 11 illustrate touch input systems within an automobile dashboard in accordance with embodiments.

FIG. 12 illustrates a user touching/tapping on a touch surface in accordance with one embodiment.

FIG. 13 is a graph of the voltage generated by the MFC actuator(s) on a touch screen vs. time in accordance with one embodiment.

FIG. 14A illustrates a single-cantilever configuration of a MFC actuator and a substrate in accordance with one embodiment.

FIG. 14B is a graph of total displacement vs. thickness of substrates with different Young's moduli.

FIGS. 15A and 16A illustrate an inner surface/underside of a touch surface in accordance with embodiments.

FIGS. 15B and 16B illustrate an outer surface/outside of a touch surface in accordance with embodiments.

FIG. 17 is a flow diagram of providing haptic feedback on a haptically-enabled device according to one embodiment.

FIG. 18 is a block diagram of a haptic system in a haptically-enabled device according to one embodiment.

DETAILED DESCRIPTION

Embodiments are directed to providing haptic feedback using an actuation system, and more particularly, to providing haptic feedback by rendering haptic effects using a high bandwidth thin actuation system Haptics is a tactile and/or kinesthetic feedback technology that generates haptic feedback effects (also known as "haptic feedback" or "haptic effects"), such as forces, vibrations, and motions, for an individual using the individual's sense of touch. A haptically-enabled device can include embedded hardware (e.g., an actuation system or other output mechanisms) configured to apply the haptic effects. The embedded hardware is, generally, programmed to apply (or playback) a particular set of haptic effects. When a signal specifying which haptic effect(s) to play is generated or received by a processor of the haptically-enabled device, the embedded hardware of the haptically-enabled device renders the specified haptic effect. For example, when an individual is intended to experience a haptic event, the embedded hardware of the haptically-enabled device receives a play command through control circuitry. The embedded hardware then applies the appropriate haptic effect.

One embodiment uses a thin actuation system, such as a Macro Fiber Composite ("MFC") actuator attached to an internal surface (or inside) of a back cover of a smartphone or other mobile device to provide deformation haptic effects, low-frequency vibratory haptic effects, and/or high definition vibratory haptic effects on the back cover of the mobile device. The actuation system can be attached by an adhesive such as an epoxy or suspension, in one embodiment. In other embodiments, the back cover itself is used as a thin actuation system to provide the haptic effects by co-molding the actuation system and the back cover.

Figure 1:
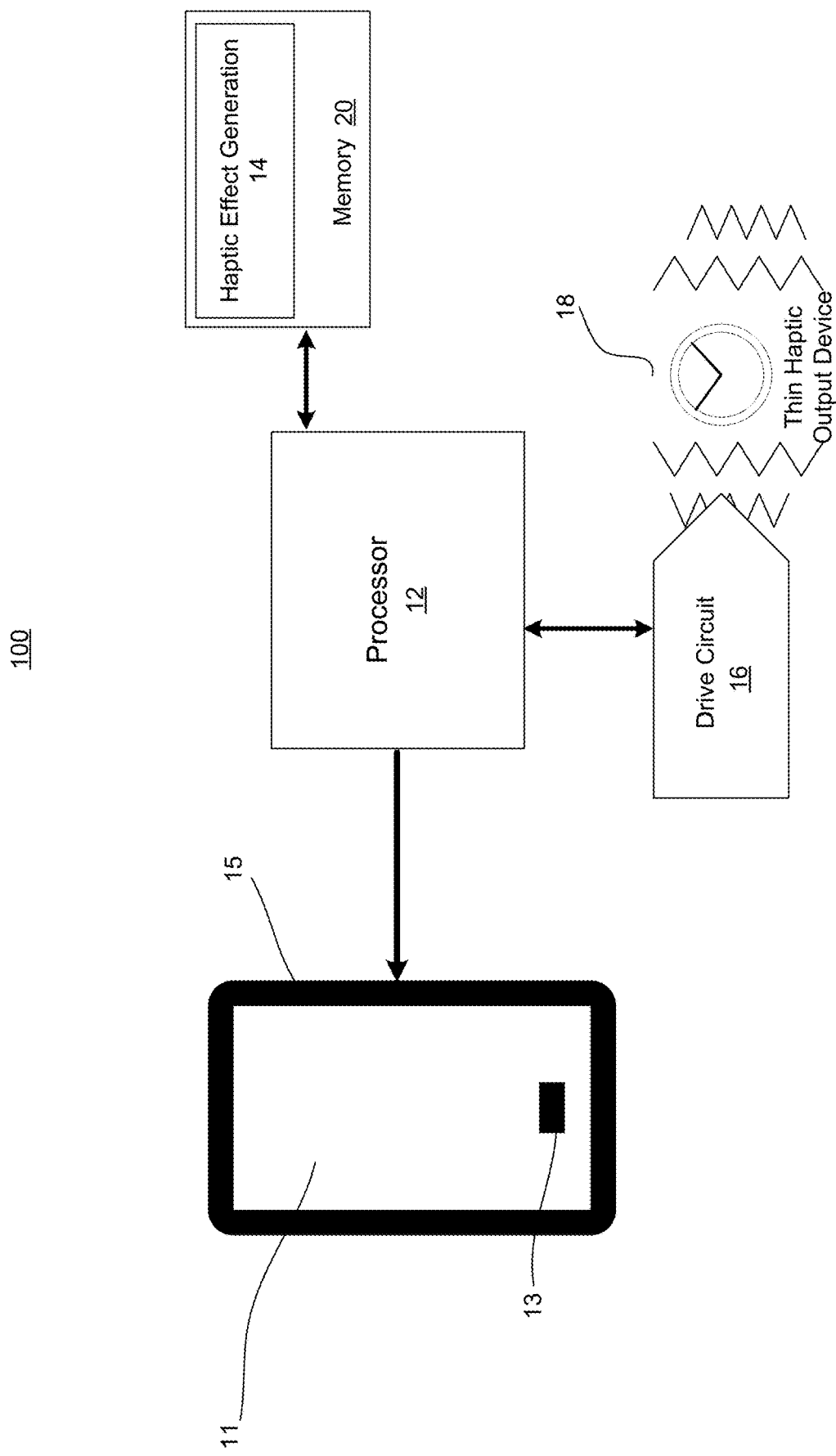
FIGS. 1-13, 14A, 14B, 15A, 15B, 16A, 16B, 17 and 18 represent non-limiting, example embodiments as described herein.

FIG. 1 is a block diagram of a haptically-enabled mobile device/system used to implement one embodiment.

Referring to FIG. 1, a haptically-enabled mobile device/system 10 includes a touch sensitive surface 11 or other type of user interface mounted within a housing 15, and may include mechanical or "soft" keys/buttons 13. Housing 15 may include two or more separate portions/parts, including a front cover or front screen, and a back cover (not shown). Internal to system 10 is a thin haptic feedback system that generates haptic effects on system 10. In one embodiment, the haptic effects are generated on the back cover of system 10. However, embodiments are not limited thereto, and therefore, the haptic effects can be generated on any other part of system 10.

The haptic feedback system includes a processor or controller 12. Coupled to processor 12 is a memory 20 and a drive circuit 16, which is coupled to a thin haptic output device 18. Processor 12 may be any type of general purpose processor, or could be a processor specifically designed to provide haptic effects, such as an application-specific integrated circuit ("ASIC"). Processor 12 may be the same processor that operates the entire system 10, or may be a separate processor. Processor 12 can decide what haptic effects are to be played and the order in which the effects are played based on high level parameters. In general, the high level parameters that define a particular haptic effect include magnitude, frequency and duration. Low level parameters such as streaming motor commands could also be used to determine a particular haptic effect. A haptic effect may be considered "dynamic" if it includes some variation of these parameters when the haptic effect is generated or a variation of these parameters based on a user's interaction.

Processor 12 outputs the control signals to drive circuit 16, which includes electronic components and circuitry used to supply thin haptic output device 18 with the required electrical current and voltage (i.e., "motor signals") to cause the desired haptic effects to be generated. System 10 can include more than one haptic output device 18, and each haptic output device 18 can include a separate drive circuit 16, all coupled to a common processor 12. Memory 20 can be any type of storage device or computer-readable medium, such as random access memory ("RAM"), read-only memory ("ROM"), flash memory or solid state memory. Memory 20 stores instructions executed by processor 12, such as operating system instructions. Among the instructions, memory 20 includes a haptic effect generation module 14 which is instructions that, when executed by processor 12, generate haptic effects based in conjunction with an application that requires haptic effects to be generated (e.g., in response to any type of events generated by an application executing on system 10). Memory 20 may also be located internal to processor 12, or any combination of internal and external memory.

In embodiments with a touch surface 11, the touchscreen recognizes touches, and may also recognize the position and magnitude of touches on the surface. The data corresponding to the touches is sent to processor 12, or another processor within system 10, and processor 12 interprets the touches and in response generates haptic effect signals. Touch surface 11 may sense touches using any sensing technology, including capacitive sensing, resistive sensing, surface acoustic wave sensing, pressure sensing, optical sensing, etc. Touch surface 11 may sense multi-touch contacts and may be capable of distinguishing multiple touches that occur at the same time. Touch surface 11 may be a touchscreen that generates and displays images for the user to interact with, such as keys, buttons, dials, etc., or may be a touchpad with minimal or no images.

System 10 may be a handheld device, or mobile device, such a cellular telephone, personal digital assistant ("PDA"), smartphone, computer tablet, gaming controller, etc., or may be any other type of device that provides a user interface and includes a haptic effect system that includes one or more haptic output devices. The user interface may be a touch sensitive surface, or can be any other type of user interface such as a physical button, mouse, touchpad, mini-joystick, scroll wheel, trackball, door knob, game pads or game controllers, etc. System 10 may be a flexible/bendable device that generates haptic effects when physically manipulated, in which case the "user interface" is the flexible/bendable portion of the device itself.

Thin haptic output device 18, disclosed in more detail below, is "thin" relative to the side profile of system 10, and is able to generate or render deformation type haptic effects (e.g., deforming the back cover of mobile device 10) and/or vibratory type haptic effects (e.g., vibrating the back cover in addition to other portions of mobile device 10). Specifically, embodiments can generate vibratory haptic effects with a strong low-frequency content (e.g., approximately 10 Hz-150 Hz) and deformation haptic effects (e.g., approximately 10 Hz or less, or 2 Hz-10 Hz). The vibratory frequency of strong low-frequency vibratory haptic effects in embodiments is approximately 10 Hz-150 Hz. The deformation haptic effects can be considered a low frequency (slower) version of a vibratory haptic effect, or it can be considered a single cycle of an expansion/movement outwards and then returning. The frequency of deformation haptic effects in embodiments is approximately 10 Hz or less. Further, embodiments can generate "high definition" ("HD") haptic effects that control thin haptic output device 18 with a haptic signal that varies the intensity of the haptic effect according to a signal encoded with a value of +/−127 for each sample of the high definition haptic signal supplied typically at 8 kHz. The vibratory frequency of HD vibratory haptic effects in embodiments is approximately 150 Hz-800 Hz. In one embodiment, narrow HD vibratory haptic effects are generated. A vibratory frequency of the narrow HD vibratory haptic effects is approximately 200 Hz.

In one embodiment, the thin haptic output device 18 can be configured to generate strong low-frequency vibratory haptic effects and HD vibratory haptic effects. In one embodiment, the thin haptic output device 18 can be configured to generate deformation haptic effects and strong-low frequency vibratory haptic effects. In one embodiment, the thin haptic output device 18 can be configured to generate deformation haptic effects, strong low-frequency vibratory haptic effects and HD vibratory haptic effects.

Some known actuators used to generate haptic effects generally cannot provide the range of haptic effects disclosed above. For example, a Linear Resonant Actuator ("LRA") or a Solenoid Resonant Actuator ("SRA") generally have a narrow band HD effect of approximately 200 Hz and an acceleration of 1 G, peak to peak ("pp"). Further, an LRA generally cannot provide low frequency content and deformation haptics. Further, the thickness of an LRA is approximately 3 mm (i.e., not "thin"), and it is not flexible. Likewise, an Eccentric Rotating Mass ("ERM") vibration motor cannot generally provide HD haptic effects content and the thickness of an ERM bar is also approximately 3 mm.

In accordance with embodiments, processor 12, memory 20, drive circuit 16 and haptic output device 18 can all be contained within the housing 15.

Figure 2:
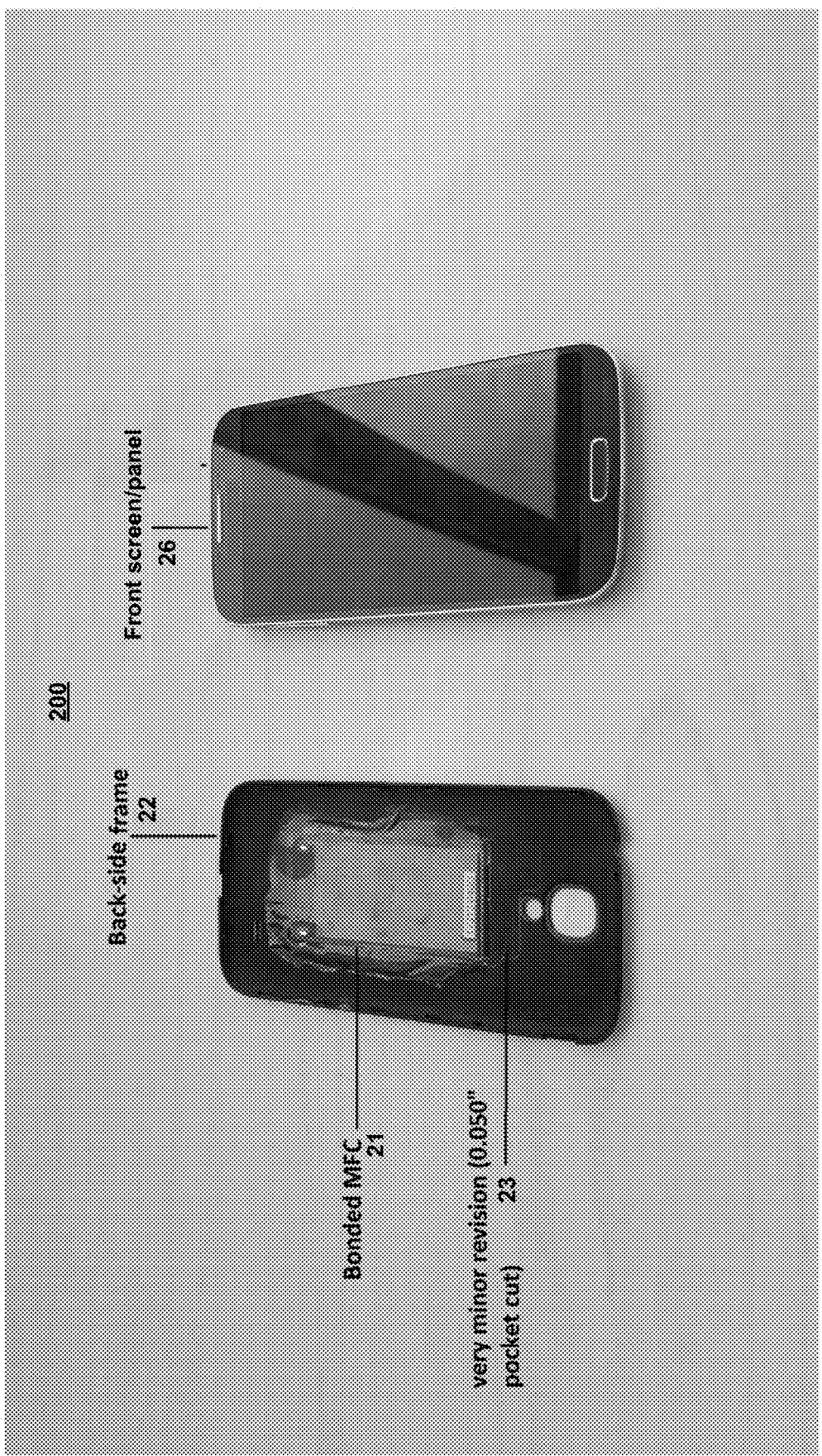

FIG. 2 illustrates a disassembled view of a mobile device in accordance with one embodiment.

Referring to FIG. 2, a mobile device 200 includes a front screen/panel 26 and a back cover/panel or back-side frame 22. Back cover 22 is a flat or generally flat surface. A Macro Fiber Composite ("MFC") actuator 21 that functions as a thin actuation system is attached to the inner surface of back cover 22 (i.e., a substrate). In one embodiment, MFC actuator 21 can be bonded to the inner surface of back cover 22 using a chemical substance such as an epoxy or an adhesive, or using a process such as soldering, brazing or welding. In one embodiment, MFC actuator 21 can be attached to the inner surface of back cover 22 using a mechanical device such as fasteners or magnets. MFC actuator 21 can be fixedly attached or removably attached to back cover 22.

In one embodiment, a pocket cut 23 of approximately 0.050" on the inside of back cover 22 allows MFC actuator 21 to be positioned substantially flush to the inside of back cover 22 and allows the overall case of device 10 to tightly fit together. Pocket cut 23 further changes the thickness of back cover 22. Further, pocket cut 23 may allow the haptic effect to be generally isolated on the back cover to the thinner portion necessitated by the pocket cut. The device driver and/or processor of device 10 is electrically coupled to MFC actuator 21.

In one embodiment, MFC actuator 21 is the "MFC M5628 P1" from Smart Material Corp. An MFC actuator, in general, is formed by rectangular piezo ceramic rods sandwiched between layers of adhesive, electrodes and polyimide film. The electrodes are attached to the film in an interdigitated pattern which transfers the applied voltage directly to and from the ribbon shaped rods. In one embodiment, the thickness of MFC actuator 21 is approximately 0.5 mm. However, embodiments are not limited thereto, and the thickness of MFC actuator 21 can be less than 0.5 mm such as 10 μm to 100 μm, approximately 10 μm or approximately 100 μm. In other embodiments, the thickness of MFC actuator 21 can be about 2 to 3 mm, about 1 to 2 mm, or less than 1 mm.

In other embodiments, a thin smart material alternative to MFC actuator 21 can be used as the actuation system.

Figure 3:
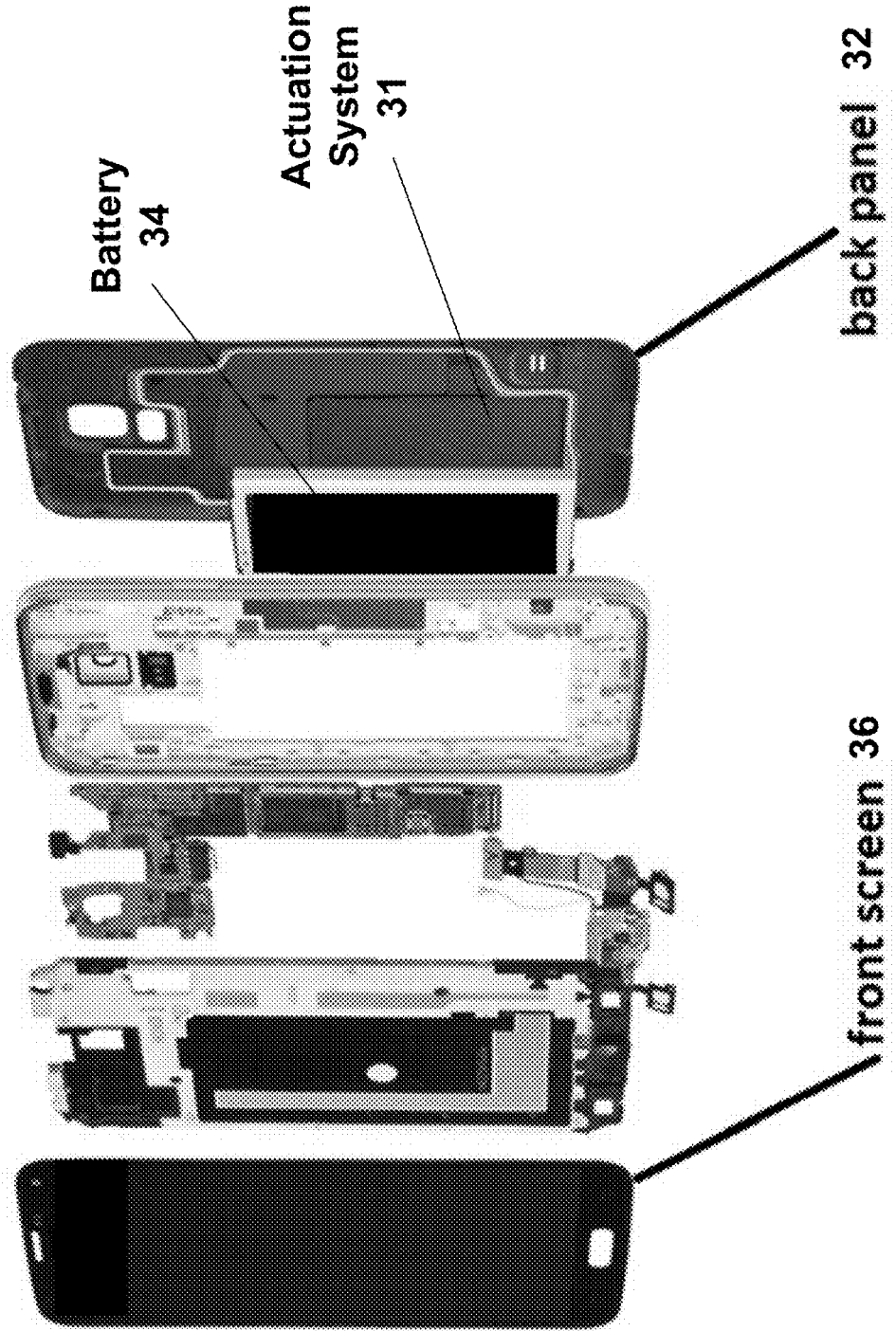

FIG. 3 illustrates an exploded view of a mobile device in accordance with one embodiment.

Referring to FIG. 3, the positioning of actuation system 31 (e.g., one or more MFC actuators) relative to a battery 34 and the other components between a front screen 36 and a back panel 32 of a mobile device 300 are shown.

As shown in FIG. 2, in one embodiment, an MFC actuator 21 is bonded to the back cover 22 of mobile device 200. In this embodiment, the back cover 22 functions as a substrate to generate three types of haptic effects as previously described: (1) wide-band HD; (2) Low-Frequency; and (3) Deformation. In other embodiments, instead of an MFC actuator, actuation system 31 as shown in FIG. 3 can be a multi-layer Electroactive Polymers ("EAP"), a polyvinylidene difluoride ("PVDF") or dielectric elastomer. In one embodiment, the front screen 26 can be formed of EAPs, PVDF or dielectric elastomers due to their flexibility. For instance, when the bend radius of the haptically-enabled device is more than 50 mm, MFC actuator 21 can be used as the actuation system 31. When the bend radius of the haptically-enabled device is less than 50 mm, EAPs, PVDF and dielectric elastomers can be used as the actuation system 31. The bend radius, which is measured to the inside curvature, is the minimum radius the haptically-enable device can be bent without kinking, damaging, or breaking. In other embodiments, actuation system 31 can be formed from smart gels or materials (such as magnetorheological fluid ("MRF")), or photo sensitive materials that respond to light or temperature.

Figure 4:
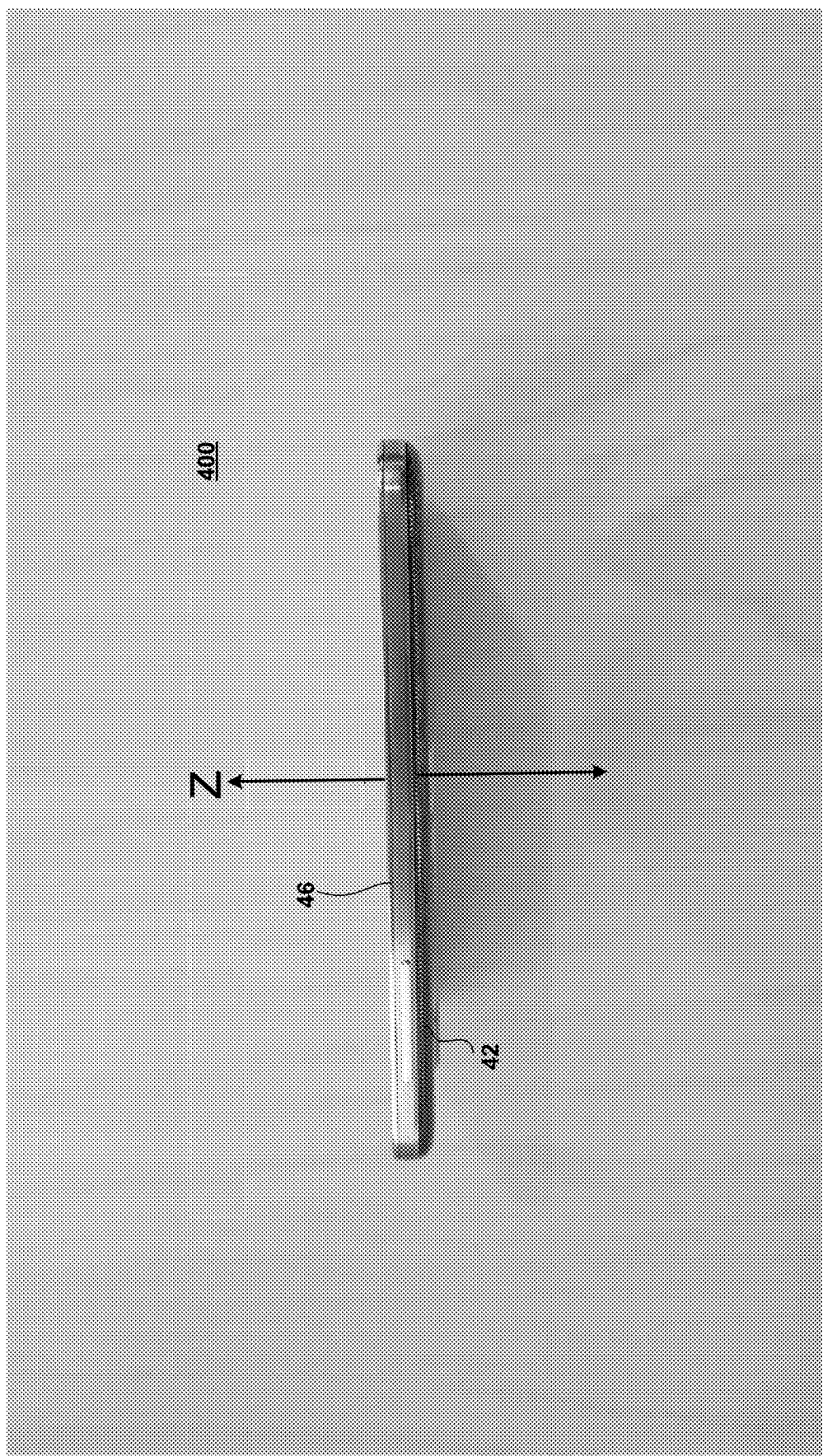

FIG. 4 illustrates a side profile view of a mobile device in accordance with one embodiment.

As shown in FIG. 4, even with the addition of a thin actuator system, back cover 42 and front screen 46 of a mobile device 400 are coupled together without any extra space required. FIG. 4 further illustrates the "z-axis" of mobile device 400, which extends perpendicular from the front screen surface and back cover surface.

Figure 5:
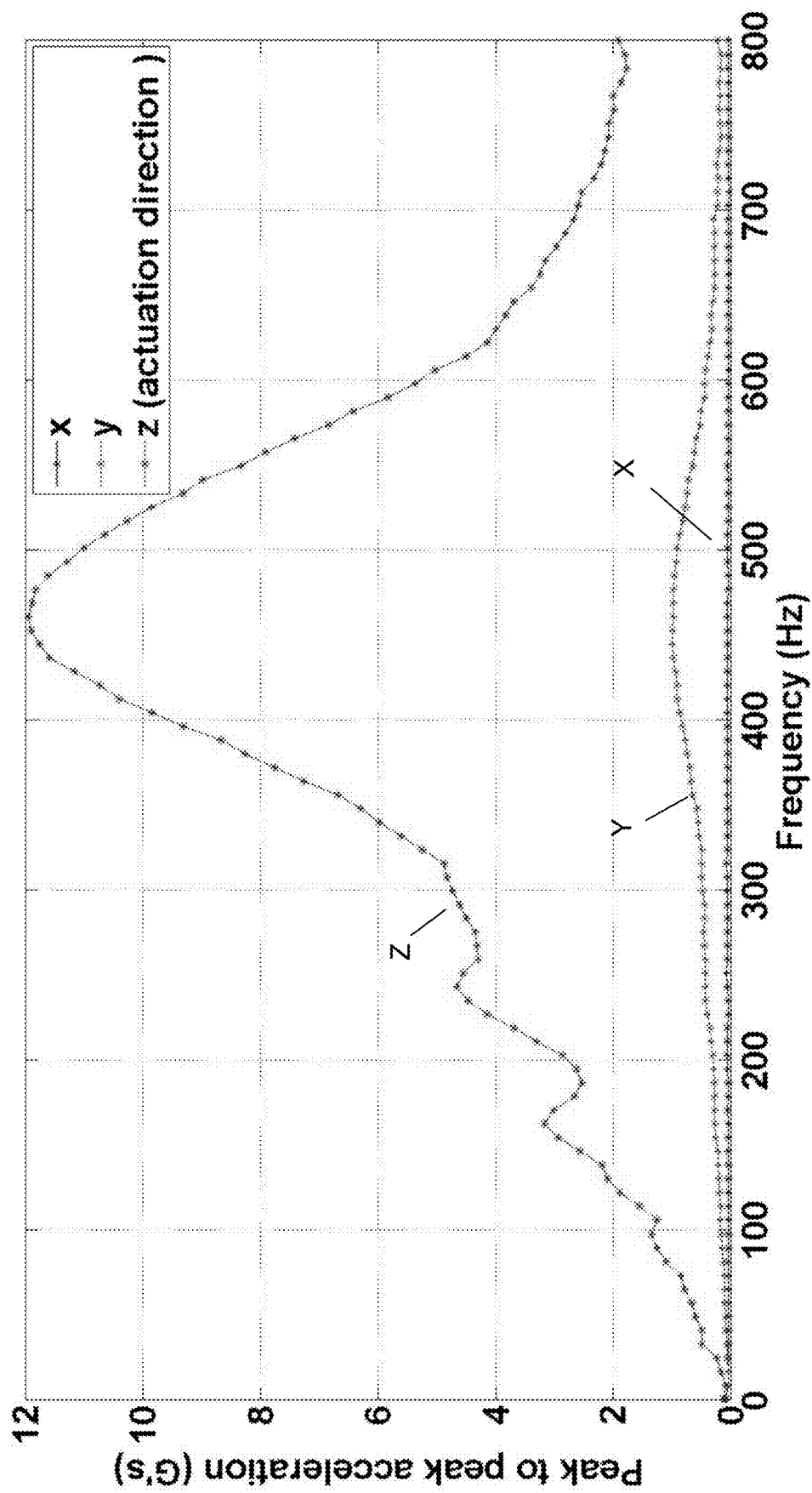

FIG. 5 is a graph of measured peak to peak acceleration on the top-side of the outer surface of a mobile device in accordance with one embodiment.

In FIG. 5, a frequency sweep for input voltage of 1500 V for 3 cycles is applied. The MFC actuator needs an electrical field to be actuated. Depending on the type of MFC actuator, in one embodiment −60 to 360 V is applied, and in another embodiment −500 to 1500 V is applied. In one embodiment, a sine wave is applied instead of a square wave since a square wave generates a substantially high audible noise. However, if audible noise is not an issue, a square wave can produce a stronger force or acceleration. Further, an arbitrary signal can be sent to the MFC actuator or other type of thin actuator, such as in a waveform containing a signal with multiple frequencies (e.g., a sound signal but with frequencies below 1000 Hz or 500 Hz). Other wave shapes are triangular, ramp up/down, frequency limited noise, white noise, pink noise, etc. The aforementioned signals, or other signals, can also be combined or superimposed to create new signals that can drive the MFC actuator. The signals can also be generated by a variety of algorithms, for instance, granular synthesis.

As shown, the acceleration (above 0.5 G peak-to-peak ("pp")) starts from 30 Hz and continues even after 800 Hz. Below 30 Hz, a user can feel deformation haptic effects to about 2 Hz. The maximum acceleration for the front side of device 10 is approximately 12 G pp.

Figure 6:
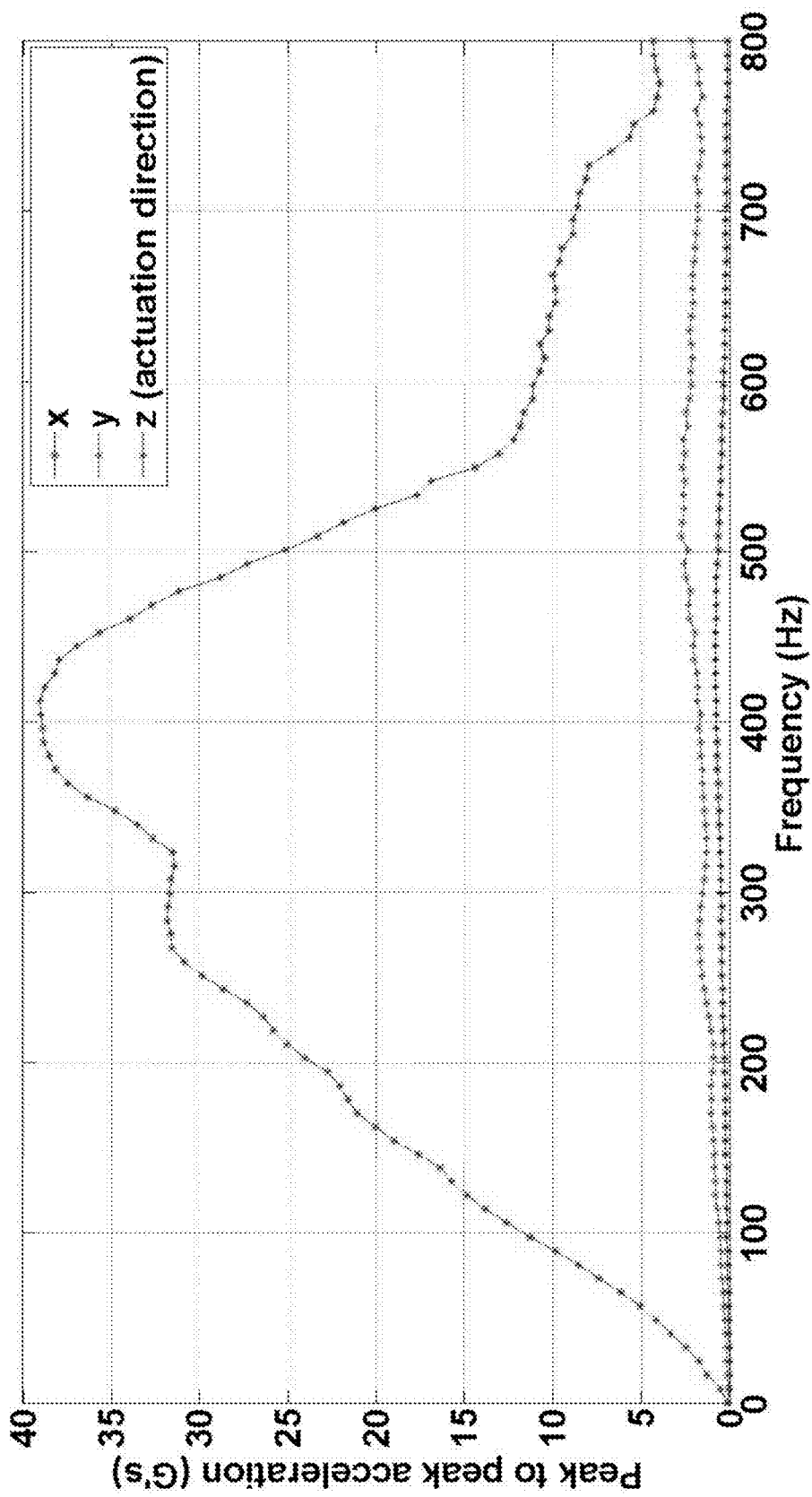

FIG. 6 is a graph of measured peak to peak acceleration on the bottom-side of the outer surface of the mobile device used to obtain the data shown in FIG. 5 in accordance with one embodiment.

In FIG. 6, similar to FIG. 5, a frequency sweep for input voltage of 1500 V for 3 cycles is applied. As shown, the acceleration (above 0.5 G pp) starts from 5 Hz and continues even after 800 Hz. The maximum acceleration on the bottom cover is approximately 40 G pp. Based on FIGS. 5 and 6, the input voltage can be dropped down to 500 V because the acceleration at 1500 V may be considered too strong for generating acceptable haptic effects. The deformation effect can be at frequencies below 5 Hz, 10 Hz, etc. The displacement of the back cover is in the order of millimeters, 1, 2, 3, or 4 mm.

FIGS. 5 and 6 demonstrate the benefits and viability of using a MFC actuator attached to the cover of a mobile device compared to other types of actuators and/or other configurations of actuators.

In another embodiment, a transparent MFC actuator is bonded under the front screen of mobile device 10 instead of, or in addition to, being bonded inside the back cover.

Figure 7:
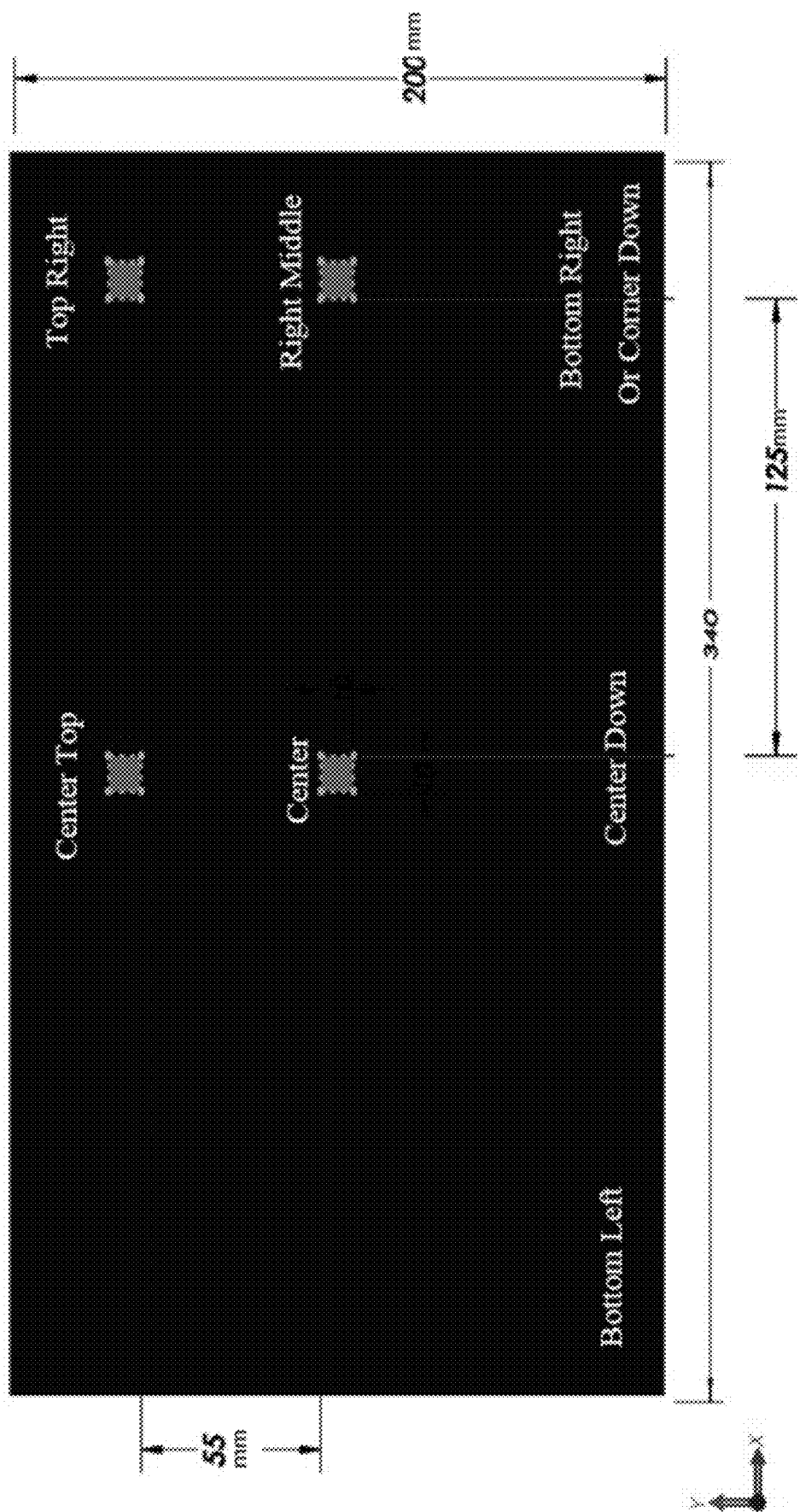
Figure 8:
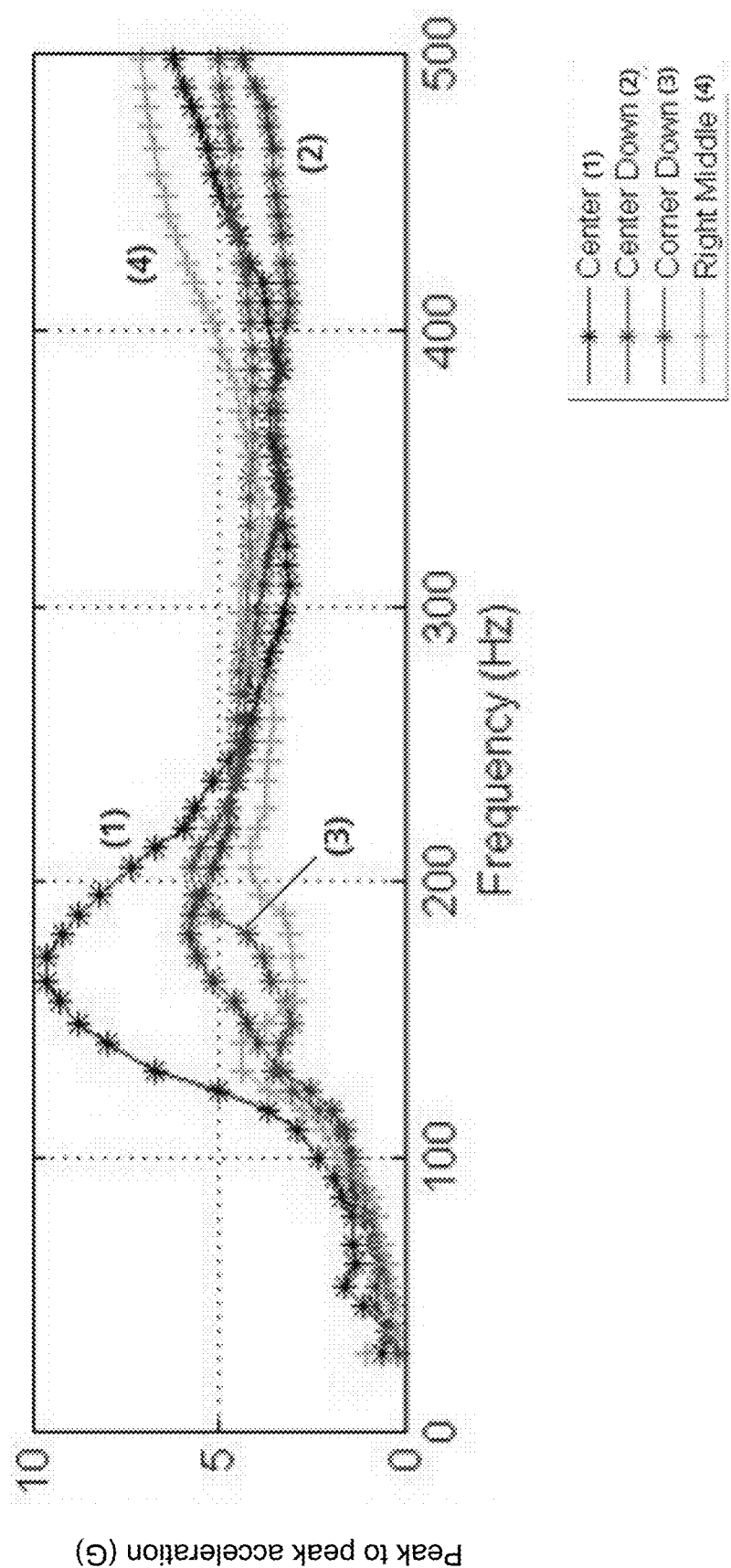
Figure 9:
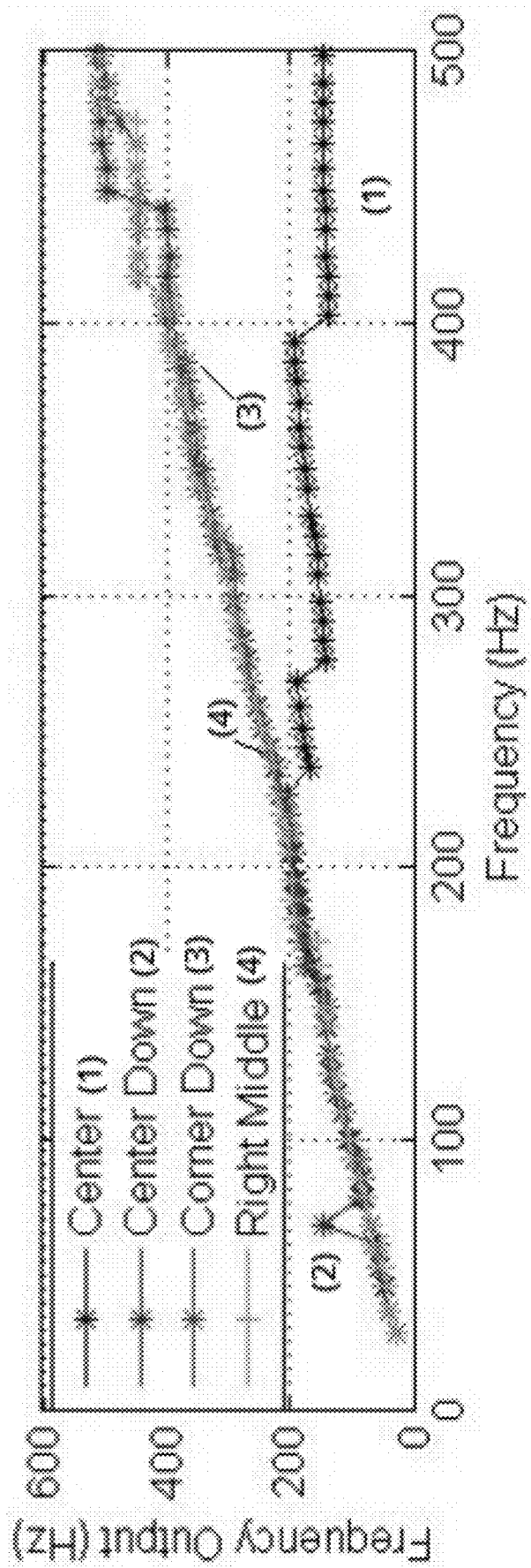

FIG. 7 illustrates reference points on a front screen for the measurements in FIGS. 8 and 9 in accordance with embodiments.

FIG. 8 is a graph of measured peak to peak acceleration vs. frequency at different reference points on a front screen of a haptically-enabled device in accordance with one embodiment.

In FIG. 8, the acceleration (above 0.5 G pp) starts from 5 Hz and continues even after 500 Hz. The maximum acceleration (approximately 10 G pp) is near the center of the front screen.

FIG. 9 is a graph of measured output frequency vs. frequency at different reference points on a front screen of a haptically-enabled device in accordance with one embodiment.

As shown in FIG. 9, the output frequency is proportional to the frequency of the haptic effect for all of the indicated reference points on the front screen, except for near the center of the front screen where the output frequency remains fairly constant for haptic effects having a frequency of about 230 Hz or greater.

Figure 15A:
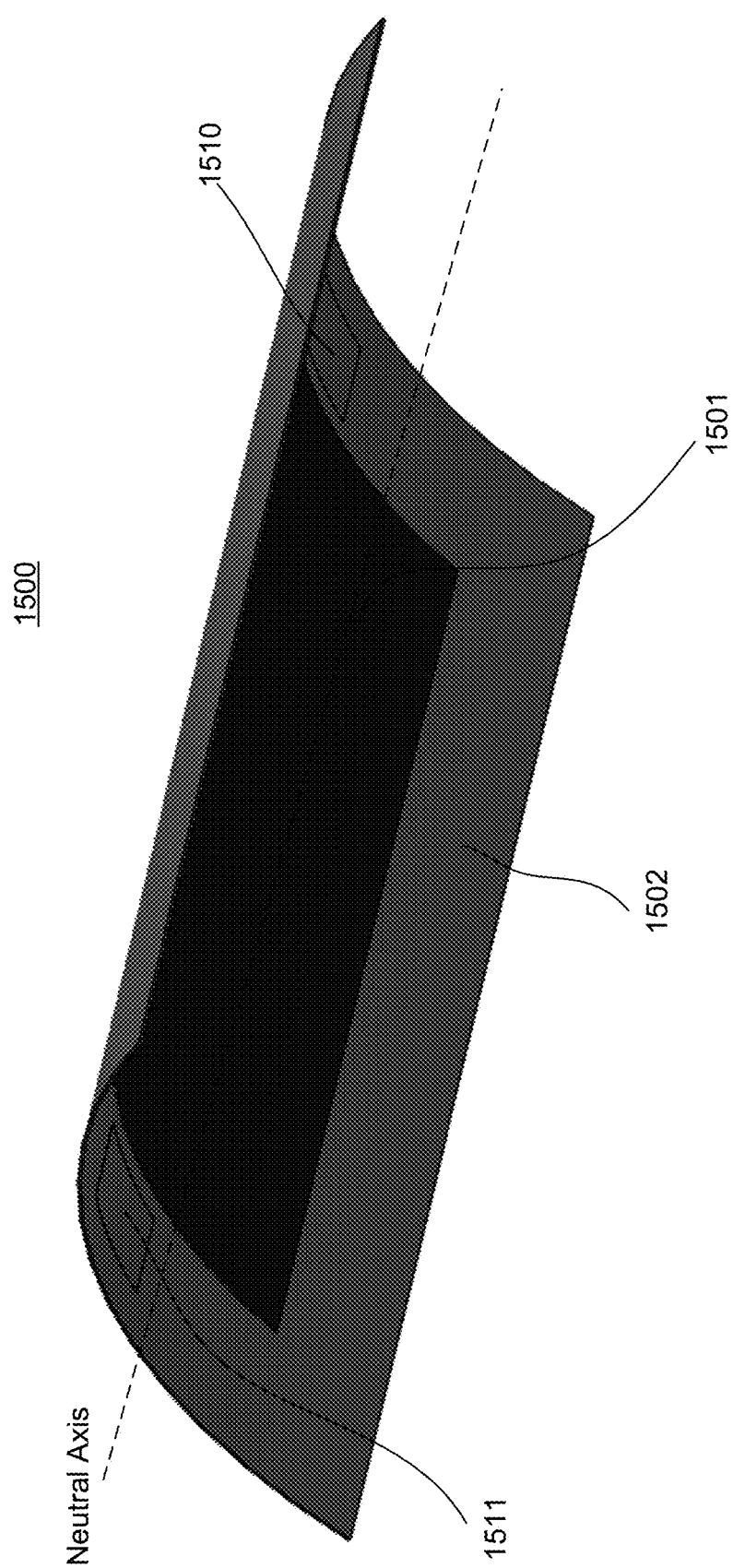
Figure 15B:
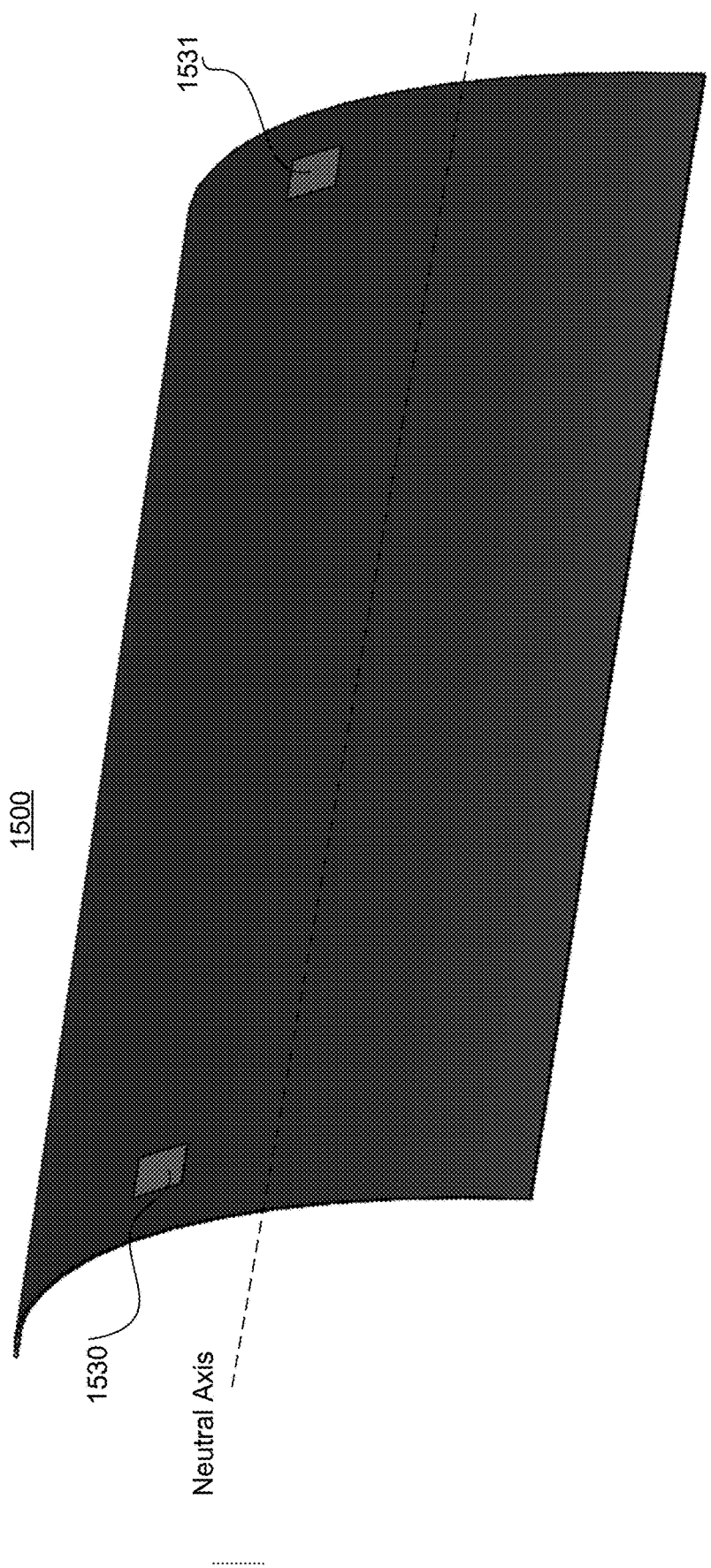
Figure 16A:
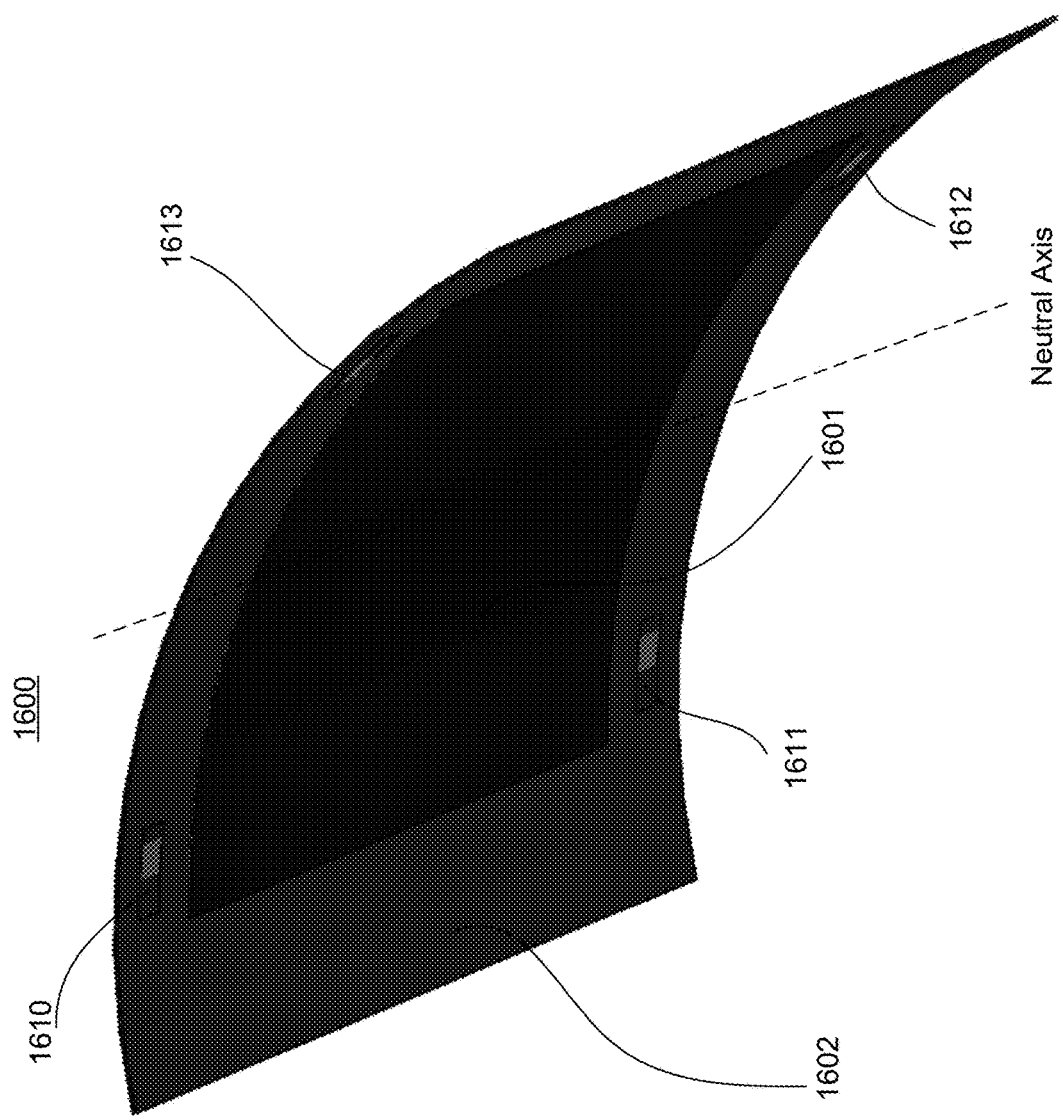
Figure 16B:
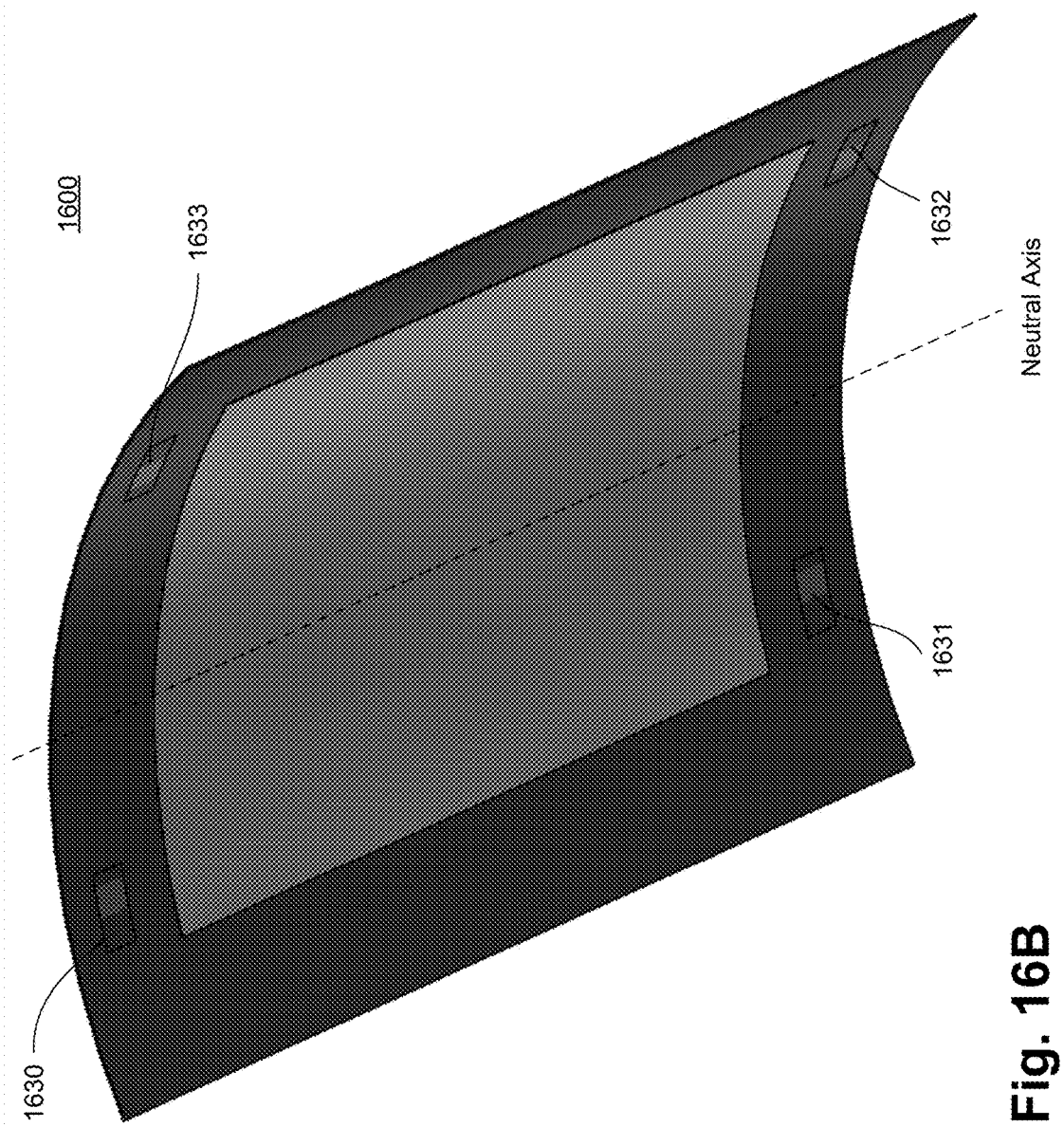

In another embodiment, multiple MFC actuators (see FIGS. 16A and 16B) are bonded to mobile device 200 at multiple locations. For examples, an MFC actuator bonded inside the back cover, another MFC actuator bonded under the screen, and third one is bonded on the edges of mobile device 200. In one embodiment, the MFC actuators are placed on different sides of a neutral axis of mobile device 200 as shown in FIGS. 16A and 16B. In other embodiments, all MFC actuators are placed on the same side of the neutral axis as shown in FIGS. 15A and 15B. The neutral axis is the geometric center of mobile device 200 when mobile device 200 is symmetric, isotropic and not curved before bending occurs. For a mobile device, in one embodiment MFC actuators are placed on the sides of the device and on the back of the device.

In another embodiment, instead of using an MFC actuator or other separate thin actuator system bonded to the inert plastic of back cover 22 or front screen 26, an actuation system can be formed within the back cover 22 or front screen 26, so that when energy is applied to back cover 22, back cover 22 or front screen 26 vibrates and/or deforms. For instance, an actuation system can be integrally-formed with back cover 22 or front screen 26 by co-molding the actuation system and back cover 22. In one embodiment, back cover 22 or front screen 26 is formed of composite materials formed through co-molding, using inert and active materials. In one embodiment, back cover 22 or front screen 26 itself can have built-in or embedded actuation capability. Back cover 22 or front screen 26 can be a composite material that is impregnated with fibers or thin sheets of material that can expand/contract, causing vibration and deformation, through back cover 22. In another embodiment, back cover 22 or front screen 26 can be formed from a co-molded woven fabric that includes threads in a certain orientation. Any other substance that expands or contracts when energized (for instance, by applying voltage) can be used in embodiments as back cover 22 or front screen 26.

In another embodiment, MFC actuator 21 or similar actuator is attached to an add-on cover that houses mobile device 200. In one embodiment, MFC actuators 21 are added to the side and the back of the add-on cover.

A suspension can be used to attach the add-on cover to the mobile device 200 to tune the dynamic behavior of the haptic feedback provided by the entire system. The suspension can be foam, gel, or smart materials such as MRF.

Attaching a suspension can help reduce the highest natural frequency from 450 Hz to 300 Hz, as shown in FIG. 5.

As disclosed, an embodiment uses a high bandwidth thin actuator bonded to the cover of a mobile device to generate multiple types of haptic effects. Using the cover itself as a substrate allows for the high bandwidth.

In other embodiments, there is a need to generate haptic effects in conjunction with larger display structures (i.e., larger than on a typical mobile device). These displays may need to conform to the substrate that they are attached to. For example, in an automobile dashboard, a display maybe be curved and may fit within a curved dashboard, which can function as a substrate. One known way to provide haptic effects to this type of display is to shake/vibrate the whole display system, using a large mass, which is not very efficient.

Figure 10:
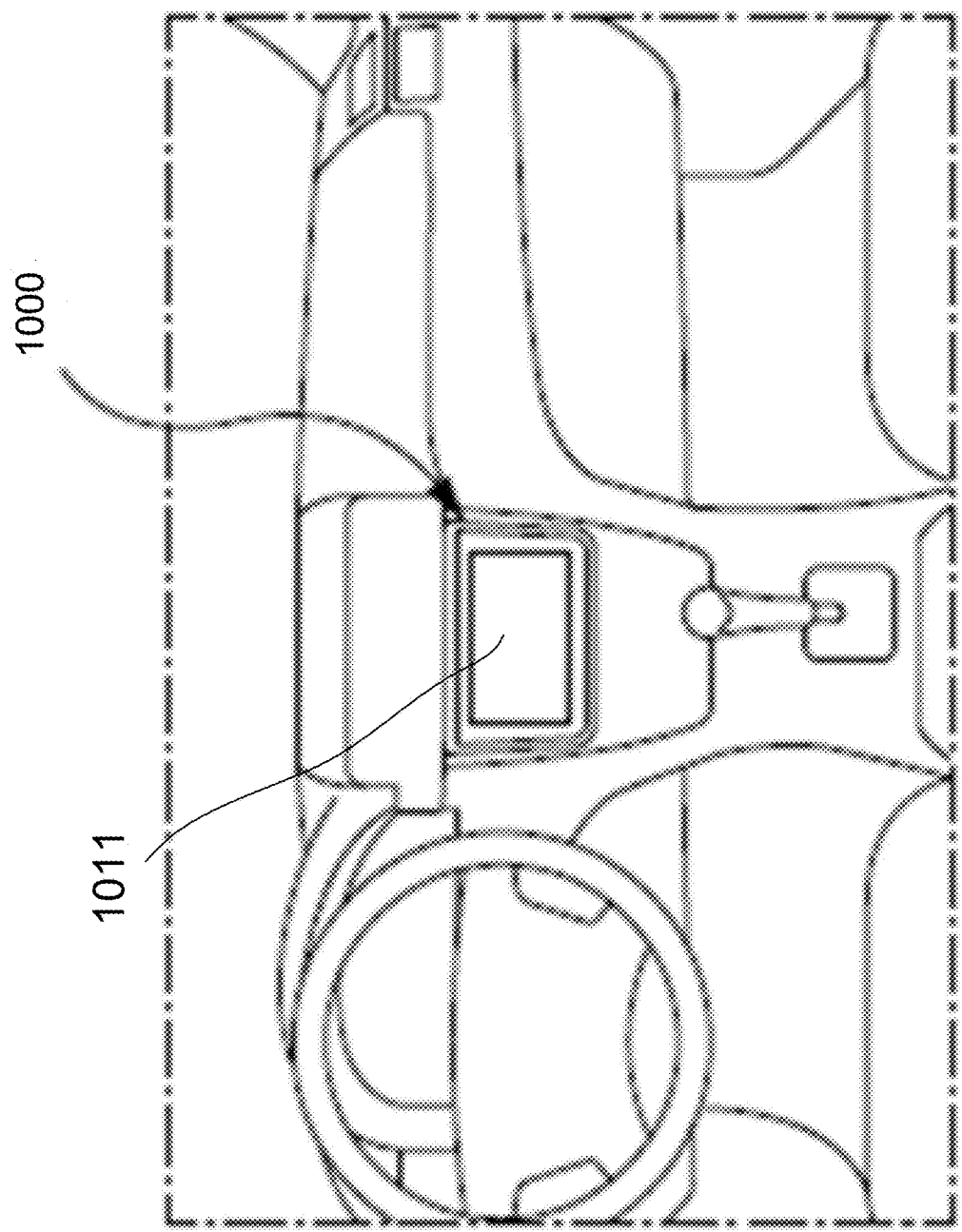

FIG. 10 illustrates a touch input system within an automobile dashboard in accordance with one embodiment.

In FIG. 10, a touch input system 1000 may be part of an in-vehicle user interface system, such as a central console system and/or vehicle dashboard system used to provide user interaction for various functionality, such as viewing and/or controlling vehicle status, cabin temperature, navigation, radio, calls and text, or other functionality. In an embodiment, the touch input system 1000 may include a touch input device 1011. The touch input device 1011 may have a front side that is a touch surface configured to receive a touch input. In an embodiment, the touch input device 1011 may include a display screen, with a surface of the screen being the touch surface. The display screen may have internal touch sensors, such as capacitive touch sensors disposed near a front side of the display screen, that configure the display screen as a touch screen, or may have no such internal sensors. In an embodiment, the touch input device 1011 may have no display screen or other display functionality, and may function as a touch pad.

In contrast, embodiments use a designed thin actuator (with a small width and a long length), such as an MFC actuator, bonded directly to a substrate in contact with the user to provide strong haptic feedback.

Figure 11:
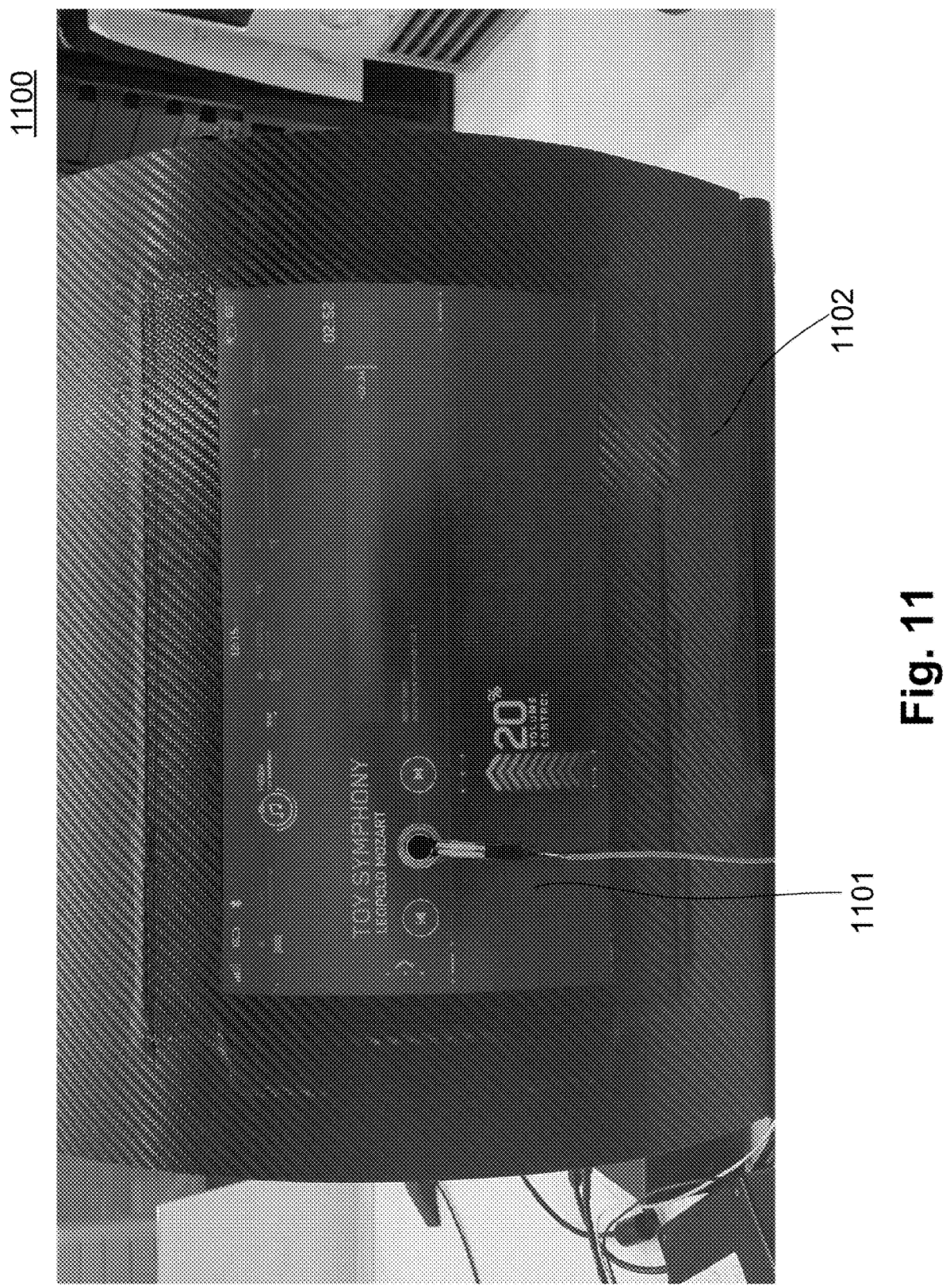

FIG. 11 illustrates a touch input system within an automobile dashboard in accordance with one embodiment.

Referring to FIG. 11, a touch input system 1100 includes a touchscreen 1101 and a surrounding substrate 1102 that may be a portion of an automobile dashboard. As shown in FIG. 11, both touchscreen 1101 and substrate 1102 are curved. System 1100 includes one or more thin actuation systems (not shown) formed from MFC actuators in one embodiment.

Referring to both FIGS. 3 and 11, in one embodiment, designed thin actuators (with a small width and a long length), such as MFC actuators, are bonded directly to a substrate, such as substrate 1102 in FIG. 11 or back panel 32 in FIG. 3, in contact with the user and provide strong haptic feedback. In other embodiments, the thin actuators are bonded on the back of a display, such as a LCD or front screen 36 in FIG. 3, or touchscreen 1101 in FIG. 11. However, the final haptic feedback or the perceived acceleration/force may be attenuated due to the multilayered structure of the LCD. Alternatively, in one embodiment, only the last element of the display structure in touch with the user actuates, which could be a glass (LCD or OLED) or plastic (OLED), without shaking/vibrating the other elements of the display. The actuator can cover the entire area or just be positioned in some locations, depending on the requirement of the haptic feedback as well as the stiffness of the substrate. In other embodiments, one or more actuators can be located at a specific location to provide localized haptic effects in the respective area.

The MFC actuator(s) directly on the front cover or the back panel of a touch screen in accordance with embodiments can function as both an actuator and a pressure sensor. The MFC actuators generate voltage as a result of being deformed. The generated voltage can be used to sense pressure applied to the front cover or the back panel to realize 3D haptic effects.

Figure 12:
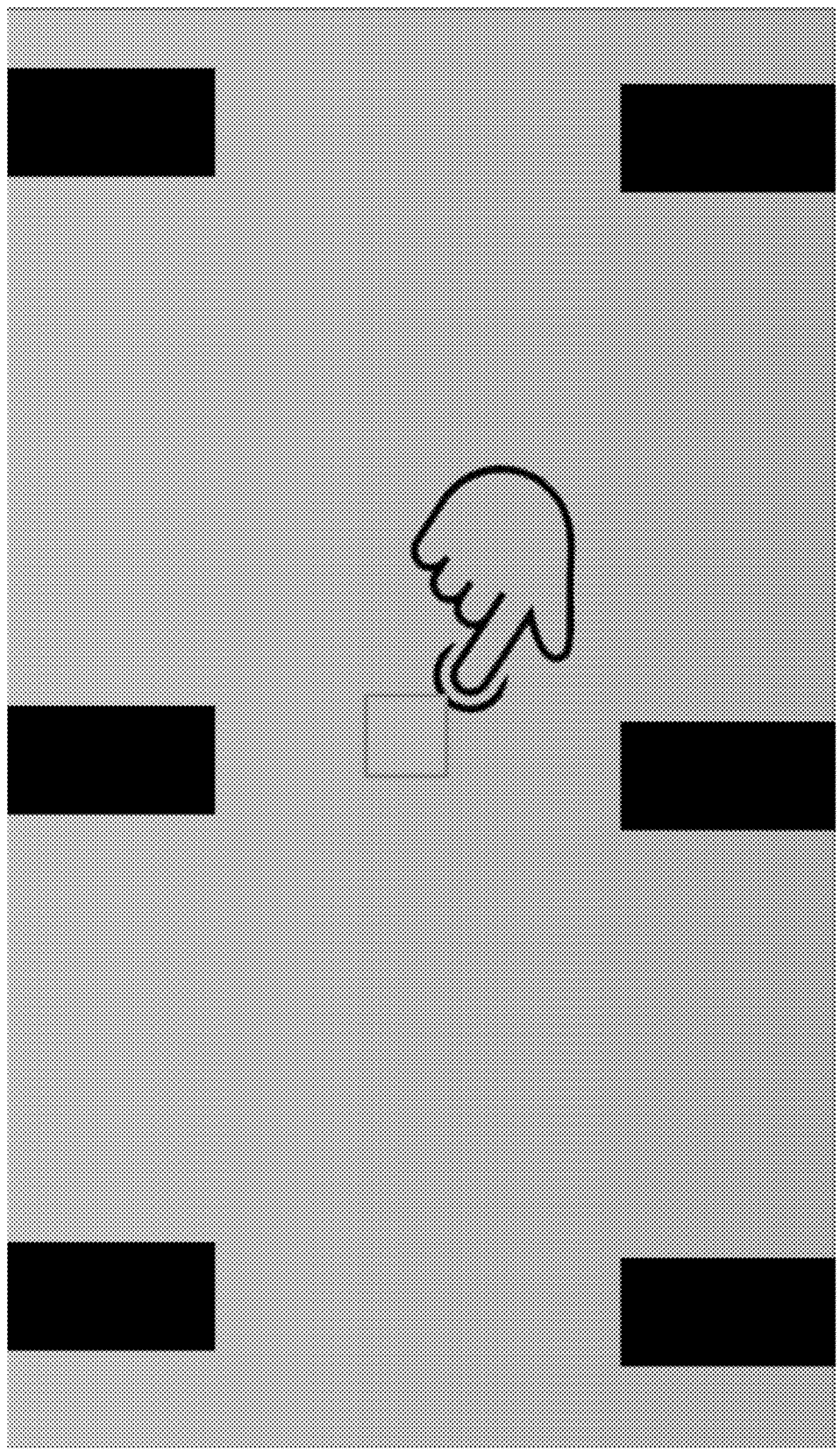

FIG. 12 illustrates a user touching/tapping on a touch surface in accordance with one embodiment.

Figure 13:
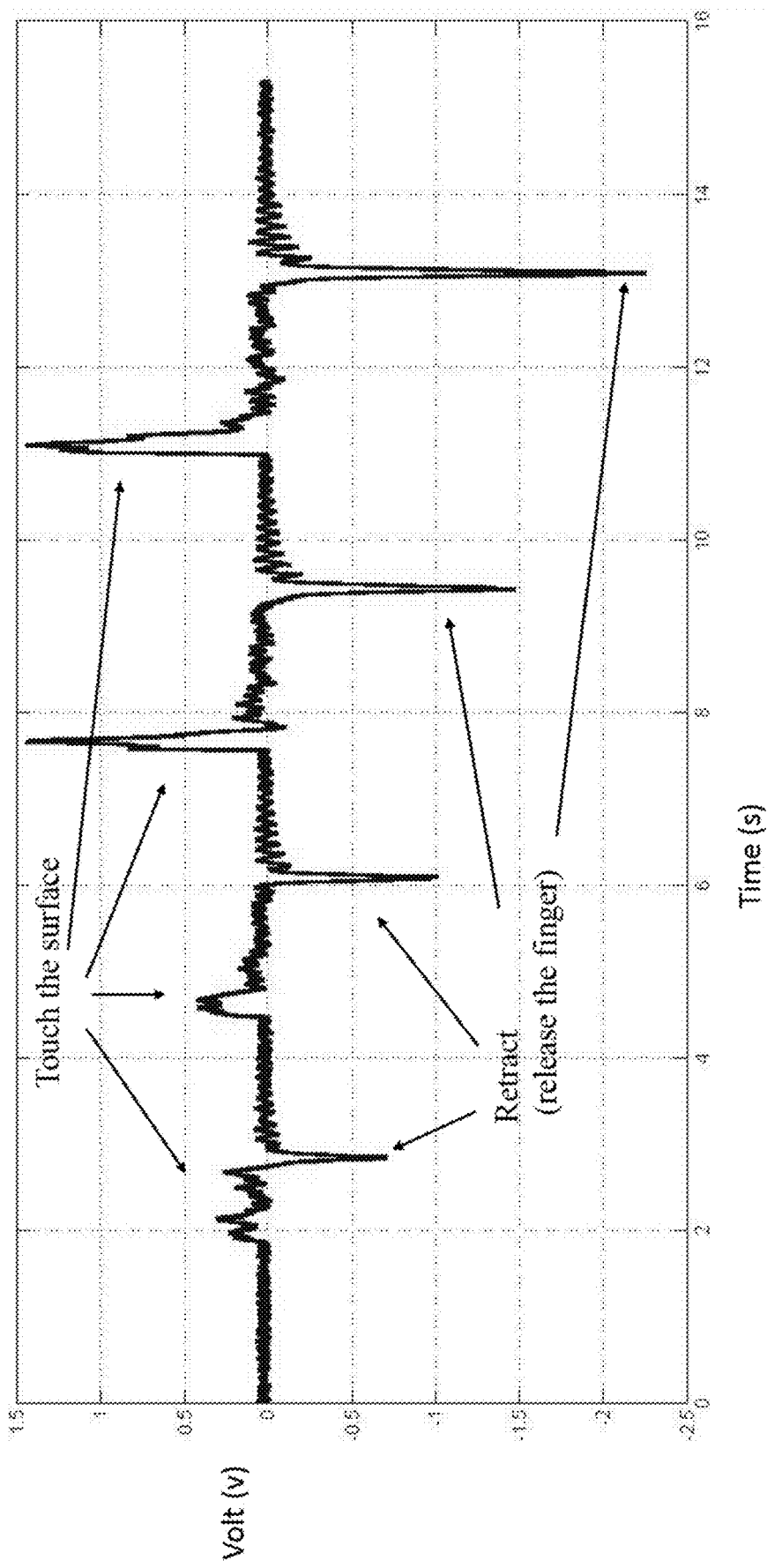

FIG. 13 is a graph of the voltage generated by the MFC actuator(s) on a touch screen vs. time in accordance with one embodiment.

As shown in FIG. 13, voltage is generated when the user applies pressure to the touch screen with the MFC actuator(s) in accordance with one embodiment.

In order to optimize haptic feedback generated using a front screen or back panel with MFC actuators in accordance with embodiments, the amplifying force (e.g., from vibratory haptic effect) or the deformation force (e.g., from a deformation haptic effect) that will be rendered by the haptic effects should be taken into consideration when determining the design and stiffness distribution of the front screen or back cover. If the amplifying forces are important, the front screen or back panel should be relatively thin, and formed of a material having a high Young's modulus such as glass fiber composite or carbon fiber composite.

Figure 14A:
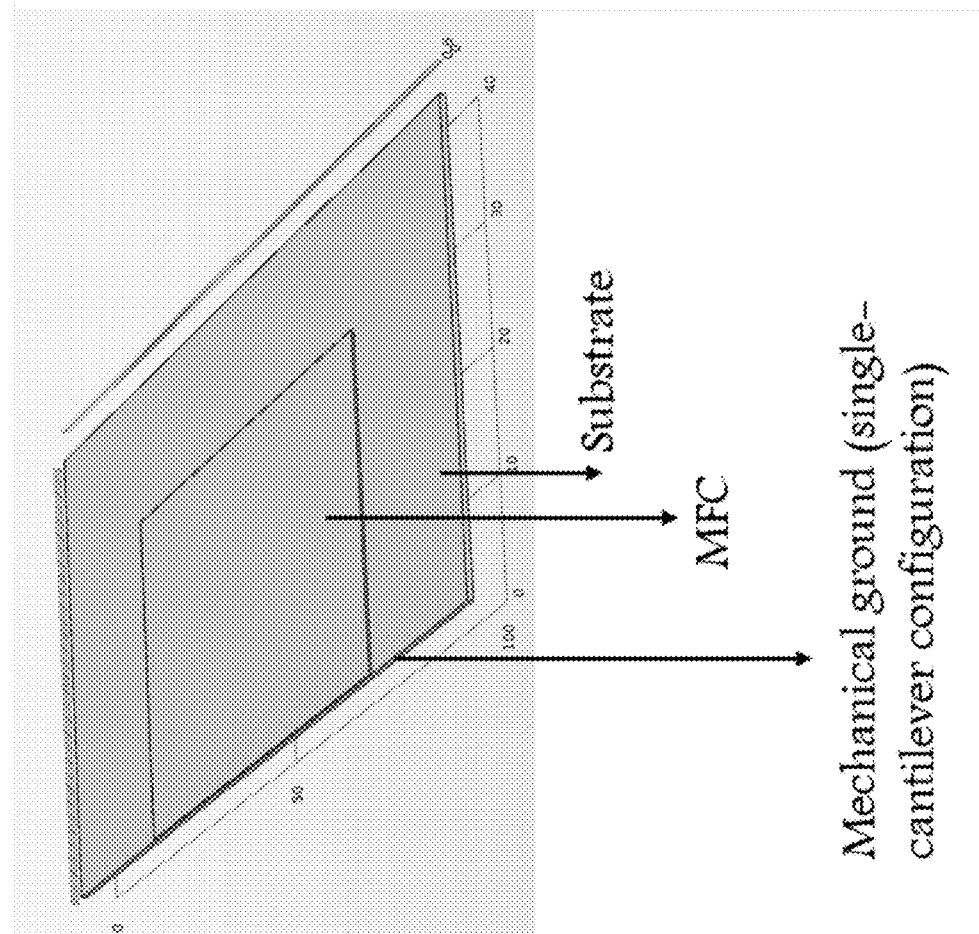

FIG. 14A illustrates a single-cantilever configuration of a MFC actuator and a substrate in accordance with one embodiment.

Figure 14B:
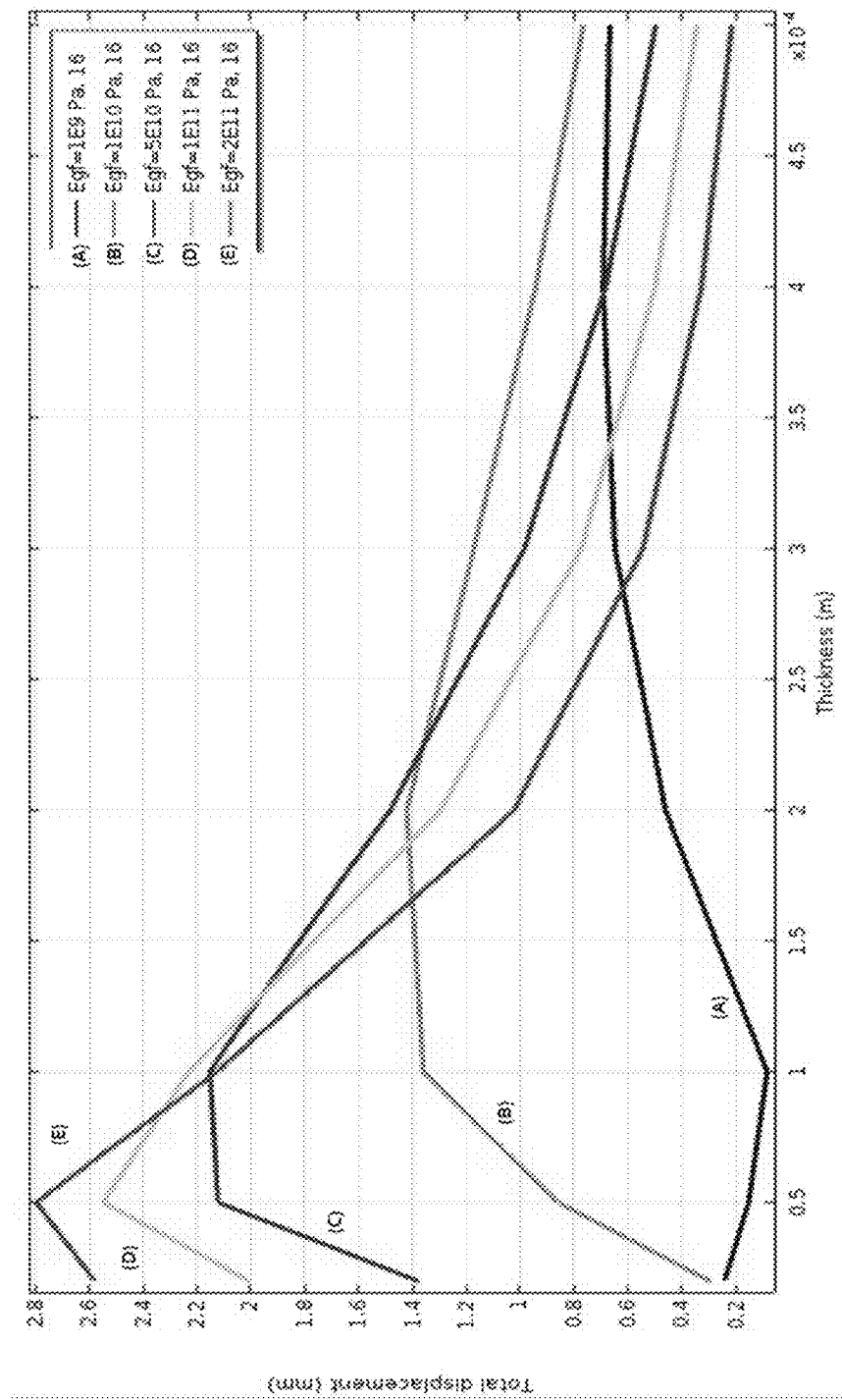

FIG. 14B is a graph of total displacement vs. thickness of substrates with different Young's moduli.

Referring to FIG. 14B, the smallest total displacement (less than 0.2 mm) was observed for substrate (A) having the lowest Young's modulus. The largest total displacement (2.8 mm) was observed for substrate (E) having the highest Young's modulus.

FIG. 15A illustrates an inner surface/underside of a touch surface in accordance with one embodiment.

FIG. 15B illustrates an outer surface/outside of a touch surface in accordance with one embodiment.

Referring to FIG. 15A, a touch surface 1500 in accordance with one embodiment includes a curved LCD or OLED touchscreen 1501, and a glass or plastic substrate 1502 implemented in an automobile dashboard. Bonded to substrate 1502 are two thin actuators/patches (e.g., MFC actuators) 1510, 1511. Actuators/patches 1510, 1511 can be on the same side of a neutral axis of touch surface 1500, as shown.

Alternatively, or in addition to the actuators/patches 1510, 1511, two additional thin actuators (e.g., MFC actuators) 1530, 1531 can be located on an outer surface of touch surface 1500, as shown in FIG. 15B.

FIG. 16A illustrates an inner surface/underside of a touch surface in accordance with one embodiment.

FIG. 16B illustrates an outer surface/outside of a touch surface in accordance with one embodiment.

Referring to FIG. 16A, an inner surface/underside of a touch surface 1600 in accordance with one embodiment includes a curved touchscreen 1601 and substrate 1602 implemented in an automobile dashboard. Bonded to substrate 1602 are four thin actuators (e.g., MFC actuators) 1610-1613. MFC actuators 1610, 1611, 1612 and 1613 are smaller than MFC actuators 1510, 1511 shown in FIG. 15A. MFC actuators 1610 and 1611 can be on a first side of a neutral axis of touch surface 1600, and MFC actuators 1612 and 1613 can be on a second side of the neutral axis of touch surface 1600.

Alternatively, or in addition to the actuators 1610, 1611, 1612 and 1613, four additional thin actuators (e.g., MFC actuators) 1630, 1631, 1632 and 1633 can be located on an outer surface of touch surface 1600, as shown in FIG. 16B.

Figure 17:
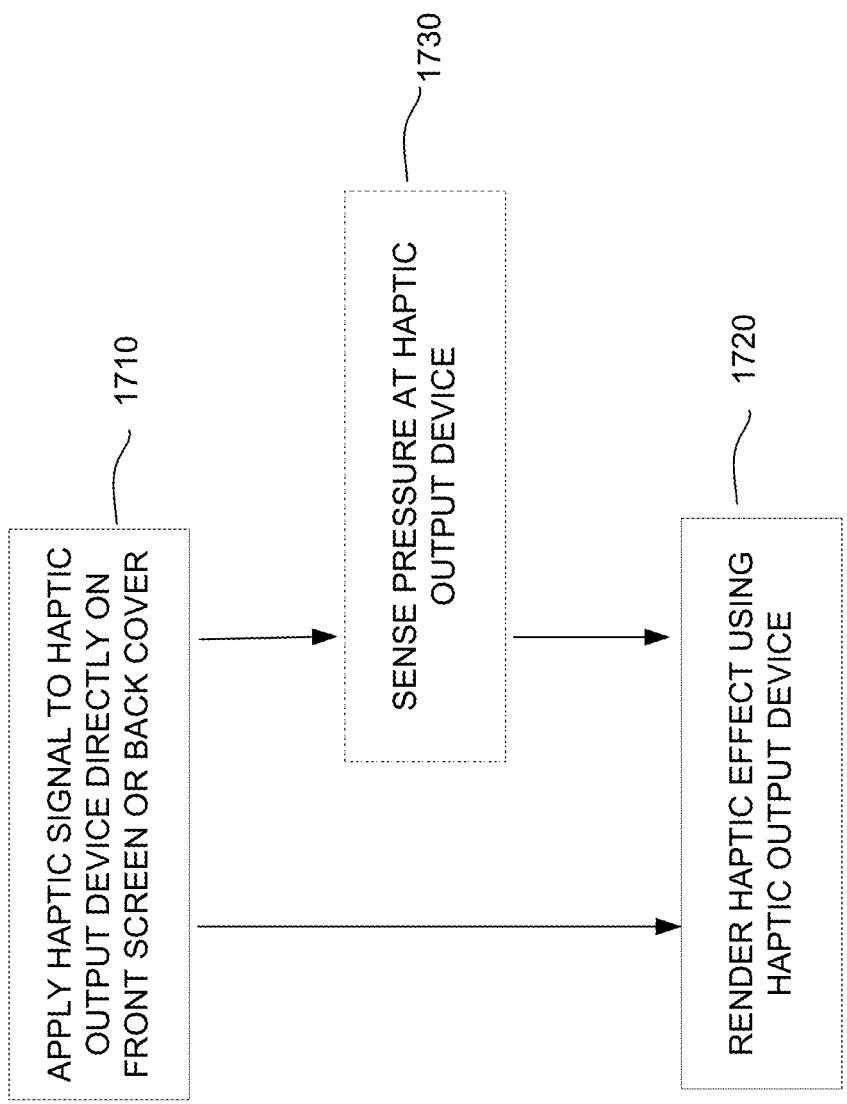

FIG. 17 is a flow diagram of providing haptic feedback on a haptically-enabled device according to one embodiment.

Referring to FIG. 17, providing haptic feedback on a haptically-enabled device according to one embodiment includes applying a haptic signal to a haptic output device, at step 1710. The haptic output device is attached to or formed within a front screen or a back cover of the haptically-enabled device. The front screen is coupled to the back cover.

At step 1720, a high-definition (HD) vibratory haptic effect, a low-frequency vibratory haptic effect or a deformation haptic effect is rendered using the haptic output device.

In one embodiment, the method further includes generating the haptic signal using a processor coupled to the haptic output device, prior to the applying of the haptic signal. The haptic output device is attached to or formed within an inner surface of the back cover. The haptic signal is applied to the haptic output device to cause the high-definition (HD) vibratory haptic effect, the low-frequency vibratory haptic effect or the deformation haptic effect to be rendered on an outer surface of the back cover.

In one embodiment, a frequency of the low-frequency vibratory haptic effect is approximately 10 Hz to-150 Hz, and a frequency of the HD vibratory haptic effect is 150 Hz-800 Hz.

In one embodiment, a frequency of the deformation haptic effect is 10 Hz or less.

In one embodiment, the haptic output device can be a Macro Fiber Composite actuator. However, as discussed above, embodiments are not limited thereto.

In one embodiment, the rendering of the haptic effect includes using a plurality of actuators directly bonded to an inner surface of the back cover. A first set of the plurality of actuators can be on a first side of a neutral axis of the back cover, and a second set of the plurality of actuators can be on a second side of the neutral axis of the back cover.

The method can optionally include, at step 1730, sensing, at the haptic output device, pressure applied to the front screen or the back cover using voltage generated from user contact to generate pressure information. The pressure information could be used to render the high-definition (HD) vibratory haptic effect, the low-frequency vibratory haptic effect and/or the deformation haptic effect as a 3D haptic effect.

Figure 18:
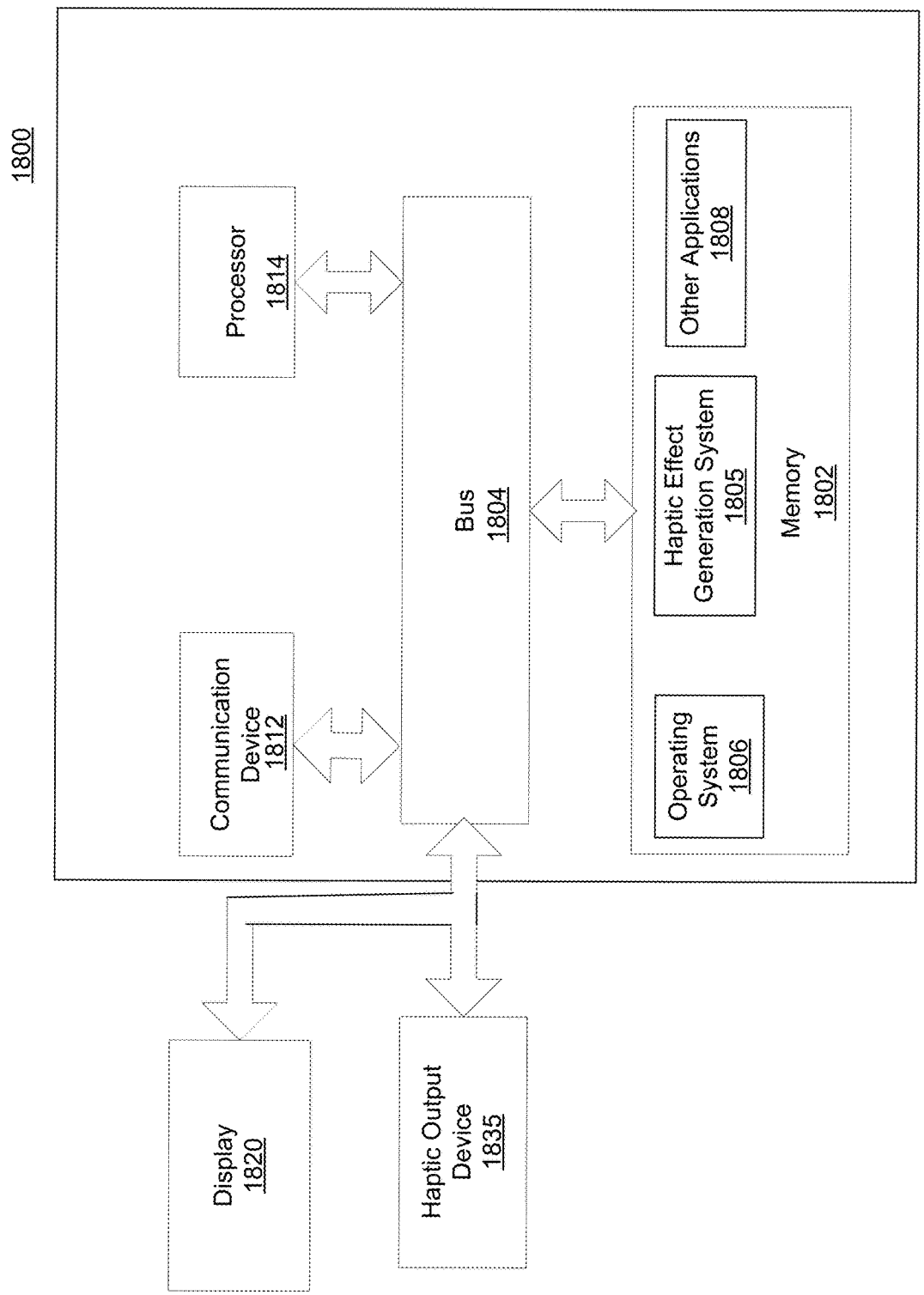

FIG. 18 is a block diagram of a haptic system in a haptically-enabled device according to one embodiment.

Referring to FIG. 18, a system 1800 in a haptically-enabled device according to an example embodiment provides haptic functionality for the device.

Although shown as a single system, the functionality of system 1800 can be implemented as a distributed system. System 1800 includes a bus 1804 or other communication mechanism for communicating information, and a processor 1814 coupled to bus 1804 for processing information. Processor 1814 can be any type of general or specific purpose processor. System 1800 further includes a memory 1802 for storing information and instructions to be executed by processor 1814. Memory 1802 can be comprised of any combination of random access memory ("RAM"), read only memory ("ROM"), flash memory, solid state memory, static storage such as a magnetic or optical disk, or any other type of non-transitory computer-readable medium.

A non-transitory computer-readable medium can be any available medium that can be accessed by processor 1814 and can include both a volatile and nonvolatile medium, a removable and non-removable medium, and a storage medium. A storage medium can include RAM, flash memory, ROM, solid state memory, erasable programmable read-only memory ("EPROM"), electrically erasable programmable read-only memory ("EEPROM"), registers, hard disk, a removable disk, a compact disk read-only memory ("CD-ROM"), or any other form of a storage medium known in the art.

According to an example embodiment, memory 1802 stores software modules that provide functionality when executed by processor 1814. The software modules include an operating system 1806 that provides operating system functionality for system 1800, as well as the rest of the haptically-enabled device. The software modules can also include a haptic system 1805 that provides haptic functionality (as described above). However, example embodiments are not limited thereto. For instance, haptic system 1805 can be external to the haptically-enabled device, for example, in a central gaming console in communication with the haptically-enabled device. The software modules further include other applications 1808, such as, a video-to-haptic conversion algorithm.

System 1800 can further include a communication device 1812 (e.g., a network interface card) that provides wireless network communication for infrared, radio, Wi-Fi, or cellular network communications. Alternatively, communication device 1812 can provide a wired network connection (e.g., a cable/Ethernet/fiber-optic connection, or a modem).

Processor 1814 is further coupled via bus 1804 to a visual display 1820 for displaying a graphical representation or a user interface to an end-user. Visual display 1820 can be a touch-sensitive input device (i.e., a touch screen) configured to send and receive signals from processor 1814, and can be a multi-touch touch screen.

System 1800 further includes a haptic output device 1835. Processor 1814 can transmit a haptic signal associated with a haptic effect to haptic output device 1835, which in turn outputs haptic effects (e.g., vibratory haptic effects and/or deformation haptic effects).

While example embodiments have been described in an automobile dashboard and a mobile device, the haptically-enable device is not limited thereto. For example, the haptically-enabled device may be a device used in a virtual reality ("VR") or augmented reality ("AR") system or in a gaming system such as a computer, a game pad or a tablet.

According to example embodiments, example embodiments use a high bandwidth thin actuator bonded to the cover of a haptically-enabled device to generate multiple types of haptic effects. Using the device itself as a substrate allows for the high bandwidth.

Several embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:
1. A haptically-enabled device, comprising:
a front screen;
a back cover coupled to the front screen; and
a haptic output device attached to or formed within the front screen or the back cover,
the haptic output device being configured to
sense pressure applied to the front screen or the back cover using voltage generated from user contact with the front screen or the back cover to generate pressure information, and
render a high-definition (HD) vibratory haptic effect, a low-frequency vibratory haptic effect, and a deformation haptic effect as a 3D haptic effect using the pressure information.

2. The haptically-enabled device of claim 1, wherein the haptic output device is a Macro Fiber Composite actuator.

3. The haptically-enabled device of claim 1, further comprising:
a processor coupled to the haptic output device, wherein the haptic output device is attached to an inner surface of the back cover, and
the processor is configured to generate a haptic signal that is applied to the haptic output device to cause the high-definition (HD) vibratory haptic effect, the low-frequency vibratory haptic effect or the deformation haptic effect to be rendered on an outer surface of the back cover.

4. The haptically-enabled device of claim 1, wherein
a frequency of the low-frequency vibratory haptic effect is approximately 10 Hz 150 Hz,
a frequency of the HD vibratory haptic effect is approximately 150 Hz-800 Hz, or
a frequency of the deformation haptic effect is approximately 10 Hz or less.

5. The haptically-enabled device of claim 1, wherein
the HD vibratory haptic effect is a narrow HD vibratory haptic effect, and
a frequency of the narrow HD vibratory haptic effect is approximately 200 Hz.

6. The haptically-enabled device of claim 1, wherein the haptic output device attached to the front screen.

7. The haptically-enabled device of claim 1, wherein
a pocket cut is on an inner surface of the back cover, and the haptic output device is directly bonded within the pocket cut.

8. The haptically-enabled device of claim 1, wherein the back cover comprises a neutral axis, and
the haptically-enabled device further comprises:
a plurality of actuators directly bonded to an inner surface of the back cover,
wherein a first set of actuators from among the plurality of actuators are disposed on a first side of the neutral axis, and a second set of actuators from among the plurality of actuators are disposed on a second side of the neutral axis, and
wherein the haptic output device is one of the plurality of actuators.

9. The haptically-enabled device of claim 1, wherein the haptic output device is integrally formed with or built-in the front screen or the back cover.

10. The haptically-enabled device of claim 1, wherein
the haptic output device is a fiber, a thin sheet or a thread,
the haptic output device expands and contracts when voltage is applied, and
the back cover is formed of a composite material including the fiber, the thin sheet or the thread.

11. A method of providing haptic feedback on a haptically-enabled device, comprising:
sensing, at a haptic output device attached to or formed within a front screen or a back cover of the haptically-enabled device, pressure applied to the front screen or the back cover of the haptically-enabled device using voltage generated from user contact with the front screen or the back cover to generate pressure information, the front screen being coupled to the back cover;

applying a haptic signal to the haptic output device, the haptic output device being configured to render to a high-definition (HD) vibratory haptic effect, a low-frequency vibratory haptic effect and a deformation haptic effect; and rendering the high-definition (HD) vibratory haptic effect, the low-frequency vibratory haptic effect or the deformation haptic effect as a 3D haptic effect using the haptic output device and the pressure information.

12. The method of claim 11, wherein the haptic output device is a Macro Fiber Composite actuator.

13. The method of claim 11, further comprising:
generating the haptic signal using a processor coupled to the haptic output device, prior to the applying of the haptic signal,
wherein the haptic signal is applied to the haptic output device to cause the rendering of the high-definition (HD) vibratory haptic effect, the low-frequency vibratory haptic effect or the deformation haptic effect on an outer surface of the back cover, and
wherein the haptic output device is attached to an inner surface of the back cover.

14. The method of claim 11, wherein
a frequency of the low-frequency vibratory haptic effect is approximately 10 Hz-150 Hz,
a frequency of the HD vibratory haptic effect is approximately 150 Hz-800 Hz, or
a frequency of the deformation haptic effect is approximately 10 Hz or less.

15. The method of claim 11, wherein
the rendering of the high-definition (HD) vibratory haptic effect, the low-frequency vibratory haptic effect or the deformation haptic effect includes using a plurality of actuators directly bonded to an inner surface of the back cover,
the back cover comprises a neutral axis, a first set of actuators from the plurality of actuators being disposed on a first side of the neutral axis, and a second set of actuators from the plurality of actuators being disposed on a second side of the neutral axis, and
the haptic output device is one of the plurality of actuators.

16. A non-transitory computer readable medium having instructions stored thereon that, when executed by a processor, cause the processor to perform operations comprising:
sensing, at a haptic output device attached to or formed within a front screen or a back cover of a haptically-enabled device, pressure applied to the front screen or the back cover using voltage generated from user contact with the front screen or the back cover to generate pressure information, the front screen being coupled to the back cover;
applying a haptic signal to the haptic output device, the haptic output device being configured to render to a high-definition (HD) vibratory haptic effect, a low-frequency vibratory haptic effect and a deformation haptic effect; and
rendering the high-definition (HD) vibratory haptic effect, the low-frequency vibratory haptic effect or the deformation haptic effect as a 3D haptic effect using the haptic output device and the pressure information.

17. The non-transitory computer readable medium of claim 16, wherein
the haptic output device is a Macro Fiber Composite actuator,
the haptic output device is attached to an inner surface of the back cover, and
the HD vibratory haptic effect, the low-frequency vibratory haptic effect or the deformation haptic effect is rendered on an outer surface of the back cover.

* * * * *